(12) United States Patent
Mercep et al.

(10) Patent No.: US 7,208,518 B2
(45) Date of Patent: Apr. 24, 2007

(54) SUBSTITUTED FUROCHROMENE COMPOUNDS OF ANTIINFLAMMATORY ACTION

(75) Inventors: Mladen Mercep, Zagreb (HR); Milan Mesic, Zagreb (HR); Boska Hrvacic, Zagreb (HR); Ivaylo Jivkov Elenkov, Zagreb (HR); Ivica Malnar, Gerovo (HR); Stribor Markovic, Zagreb (HR); Lidija Simicic, Zagreb (HR); Andreja Cempuh Klonkay, Zagreb (HR); Anita Filipovic, Zagreb (HR)

(73) Assignee: GlaxoSmithKline Istrazivacki Centar Zagreb D.O.O., Zagreb (HR)

( * ) Notice: Subject to any disclaimer, the term of this patent is extended or adjusted under 35 U.S.C. 154(b) by 0 days.

(21) Appl. No.: 11/338,871

(22) Filed: Jan. 23, 2006

(65) Prior Publication Data
US 2006/0148890 A1  Jul. 6, 2006

Related U.S. Application Data

(63) Continuation of application No. PCT/HR2004/000020, filed on Jul. 22, 2004.

(30) Foreign Application Priority Data

Jul. 25, 2003 (HR) .............................. P 20030603 A

(51) Int. Cl.
*C07D 495/14* (2006.01)
*C07D 495/04* (2006.01)
*A61K 31/352* (2006.01)

(52) U.S. Cl. ...................... 514/453; 514/455; 549/279; 549/282

(58) Field of Classification Search ............... 549/276, 549/282, 279; 514/453, 455
See application file for complete search history.

(56) References Cited

U.S. PATENT DOCUMENTS

| 4,200,577 A | 4/1980 | Buckle et al. |
| 4,263,299 A | 4/1981 | Buckle et al. |
| 4,731,375 A | 3/1988 | Nakano et al. |
| 5,428,038 A | 6/1995 | Chatterjee et al. |
| 6,100,409 A | 8/2000 | Trkovnik et al. |

FOREIGN PATENT DOCUMENTS

| EP | 0694257 | 1/1996 |
| EP | 0906909 | 4/1999 |
| WO | WO-92/13872 | 8/1992 |
| WO | WO-92/13873 | 8/1992 |
| WO | WO-94/13690 | 6/1994 |
| WO | WO-94/14834 | 7/1994 |
| WO | WO-03/029237 | 4/2003 |

OTHER PUBLICATIONS

Zhao, H et al., "Coumarin-Based Inhibitors of HIV Integrase" J. Med. Chem. 1997, 40, 242-249.
Desai, N.J. et al., "Synthesis of Some 4-Hydroxycoumarin Derivatives" J. Org. Chem. 1957, vol. 22, pp. 388-390.
Sonn, A., Ber. 1917, 50, pp. 1292-1305.
Buckle, D. et al., "Antiallergic Activity of 4-Hydroxy-3-nitrocoumarins" Journal of Medicinal Chemistry, 1975, vol. 18, No. 4, pp. 391-394.
Boyd, J. et al., J. Med. Soc. "The Chemistry of the "Insoluble Red" Woods. PartII. A New Synthesis of 4-Hydroxycounarins." 1948, pp. 174-176.
Hermodson, M. et al., Journal of Medicinal Chemistry, "Studies on the 4-Hydroxycoumarins. Synthesis of the Metabolites and Some Other Derivatives of Warfarin". 1971, vol. 14, No. 2, pp. 167-169.
Appendino, G. et al., J. Nat. Prod. "A Straightforward Entry into Polyketide Monoprenylated Furanocoumarins and Pryranocoumarins" 1999, 62, pp. 1627-1631.

*Primary Examiner*—Bernard Dentz
(74) *Attorney, Agent, or Firm*—J. Michael Strickland

(57) ABSTRACT

The present invention relates to novel compounds of the formula (I)

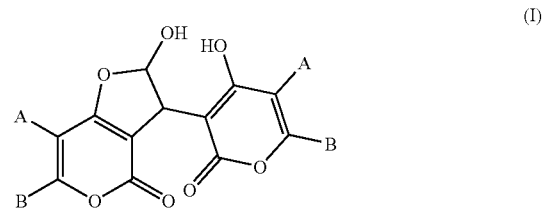

(I)

including all stereoisomers and tautomers thereof, to the pharmaceutically acceptable salts and solvates thereof, to the processes and reactive intermediates for their preparation and to their use in the prophylaxis and treatment of asthma and other inflammatory diseases and/or conditions in humans.

10 Claims, No Drawings

SUBSTITUTED FUROCHROMENE COMPOUNDS OF ANTIINFLAMMATORY ACTION

This application is a continuation of PCT International Patent Application No. PCT/HR2004/000020, filed Jul. 22, 2004, which claims priority of Croation Patent Application No.P20030603A, filed Jul. 25, 2003.

FIELD OF THE INVENTION

The present invention relates to novel compounds of the formula (I)

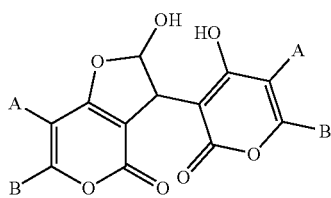

including all their stereoisomers and tautomers, to their pharmaceutically acceptable salts and solvates, to processes and reactive intermediates for the preparation thereof as well as to their therapeutical action and to their use in the prophylaxis and treatment of asthma and other diseases and/or conditions resulting from disorders of immunological system in humans.

BACKGROUND OF THE INVENTION

Asthma is a chronic inflammatory disease of respiratory airways in humans. Clinically, in hypersensitive persons the inflammation causes periodical fits of coughing, difficulties in breathing, wheezing, tightness in the chest and chest pain. Inflammation makes respiratory airways more sensitive to irritation caused by allergens, chemical irritants, tobacco smoke, cold air and effort. Respiratory airways subjected to these irritants become oedematous, contracted, filled with mucus and hypersensitive.

The pathogenesis of asthma is complex and includes the interaction of inflammatory cells, mediators as well as of the tissue and cells of respiratory airways. In asthmatic process an early phase and a late phase of response are distinguished. Allergic diseases as well as allergen-induced asthma are characterised by the synthesis of a specific type of IgE antibody. Immediately after the inhalation of allergens, complexes of allergens and allergen-specific IgE's are bound to a high affinity IgE receptor (Fcε receptor type I) present on basophils, mastocytes and eosinophils. By the binding to the receptor an activation of signal transfer cascade occurs, which results in:
1. de novo synthesis of proinflammatory genes (e.g. interleukin-4 and interleukin-5),
2. exocytosis of the content of cytoplasm granules—degranulation.

The granules contain inflammatory mediators such as histamine, serotonin, leukotrienes C4, D4 and E4, and proteins such as major basic protein and mieloperoxidase. These inflammatory mediators co-operate in the processes of vasodilation, bronchoconstriction, triggering and control of the inflammatory process and activation of the cells and damage to the inflamed tissue. These processes form the early asthmatic response. The inhibition of degranulation may prevent the symptoms and arrest the inflammation progress, which has been proven by the clinical use of degranulation inhibitors (sodium chromoglycate, nedochromyl sodium and ketotifen).

The late asthmatic response includes a permanent obstruction of air passages, a hyperactivity of the bronchi and a development of inflammation changes including the accumulation of neutrophils, eosinophils, lymphocytes and monocytes/macrophages in the respiratory system. The accumulation of inflammatory cells results from a harmonized interaction of lymphokines (TNF-α, IL-4, IL-5), adhesion molecules on the surface of leukocytes (integrins) and endothelial cells (selectins), and of chemokines (eotaxin, RANTES). The role and significance of T-lymphocytes in asthma were confirmed by the existence of an increased number of activated CD4+ T-cells in bronchoalveolar lavage and in bronchial biopsies of patients suffering from asthma. Two subpopulations of CD4+ cells differ with regard to the profile of cytokines they secrete. Th 1 cells secrete IL-2, IL-3, GM-CSF, INF-γ. An activation of Th 1 cells is important in the defence of the host against intracellular organisms, viruses and neoplasms. Investigations have demostrated that, in asthma, the Th 2 cell response prevails with an increased expression of IL-5 that is important in the formation of eosinophilic infiltration typical of allergic inflammation.

Morphologic changes occurring in asthma include an infiltration of the bronchi by inflammation cells (mastocytes, T-lymphocytes and eosinophils are the key executive cells), a clogging of respiratory airways by a secrete, interstitial oedema and increased microcirculation permeability. On the basis of pathohistological findings it has been established that eosinophil infiltration is specific and differentiates asthma from other types of inflammation.

In the control of asthma two types of medicaments exist, symptomatic ones and basic ones. The symptomatic medicaments include short-acting bronchodilators such as β2-agonists, anticholinergics, theophilin, which rapidly relax the contracted respiratory airways and alleviate the acute symptoms. The basic medicaments include antiinflammatory drugs and long-acting bronchodilators. Antiinflammatory drugs alleviate and prevent the inflammation reaction and they include inhalation corticosteroids, systemic corticosteroids, and inhalations of sodium chromoglycate and of nedochromil sodium.

Steroid antiinflamatory compounds are still considered to be the most effective medicaments in the treatment of inflammatory diseases and conditions such as asthma. The good potency and efficacy of said type of medicaments are, however, accompanied by numerous undesired side effects such as disturbances of carbohydrate metabolism, of calcium resorption, of the secretion of endogeneous corticosteroids and of physiological functions of the hypophysis, of the suprarenal gland core and of the thymus. In the literature (WO 94/13690, WO 94/14834, WO 92/13872 and WO 92/13873) so-called "soft" steroids or hydrolysable corticosteroids with local action are described. Their systemic, undesired effect is reduced due to the instability of the "soft" steroids in serum, where the active steroid is rapidly hydrolyzed to an inactive form. However, a steroid without negative side effects in long-term use still has to be found.

Some compounds of coumarin class (U.S. Pat. Nos. 4,200,577; 4,263,299; 4,731,375; 5,428,038) show antiallergic action in the prevention and treatment of various allergic diseases such as allergic asthma, allergic dermatitis, allergic rhinitis or enteritis, allergic conjunctivitis or allergic eczema.

There are also known more complex dimer and tetramer derivatives of hydroxycoumarin asymmetrically bound by a central alkyl or aryl linker, which demonstrate anti-HIV action (Zhao, H. et al., *J. Med. Chem.* 1997, 40, 242–249). Similar anti-HIV action is also shown by several products of condensation of hydroxycoumarins possessing more than one hydroxy group per coumarin unit with aromatic or aliphatic mono- or dialdehydes (U.S. Pat. No. 6,100,409 and WO 03/029237).

SUMMARY OF THE INVENTION

Compounds that are the most similar to the ones of the present invention are described in WO 03/029237 and relate to 3-(4,7-dihydroxy-2-oxo-2H-chromene-3-yl)-7-hydroxy-2,3-dihydro-furo[3,2-c]chromene-4-ones, wherein the C/2 position of the furan ring is substituted with a methoxy or ethoxy group. Said compounds are prepared by condensation of corresponding hydroxycoumarins and glyoxal in an alcohol-water medium at high temperatures, whereat in the course of the reaction a simultaneous binding of the alcohol and the formation of a corresponding alkoxy substituent occur.

By performing the reaction of condensation of hydroxycoumarin and glyoxal in the reaction medium without the presence of an alcohol, the undesired formation of alkoxy substituent in C/2 position of the furan ring is prevented and thus in this position a hydroxy substituent as an essential constituent part of the compounds of the formula (I), which are an object of the present invention, is formed.

According to our knowledge and the established prior art, compounds possessing a hydroxy group in the furan ring in C/2 position and wherein the coumarin rings, in addition to or instead of hydroxy groups, are substituted with other substituents such as alkyl and alkoxy groups or halogen atoms, which are represented by formula (I), as well as their pharmaceutically acceptable salts and pharmaceutical preparations including them in their composition, have hitherto not been described. In particular, there have not been described compounds, wherein the coumarin rings are fused with other simple or substituted aromatic or heterocyclic rings, which are also represented by formula (I) and represent an object of the present invention. Likewise, the compounds of the present invention have not been described as substances with a strong antiinflammatory action or as effective agents in the prophylaxis and treatment of asthma and other inflammatory diseases and conditions.

The applied in vitro and in vivo models quite successfully demonstrate the pathophysiological occurences present in asthma and it can be anticipated that the substances tested in these models will also be effective in the therapy of human diseases.

The present invention particularly relates to new compounds of the formula (I)

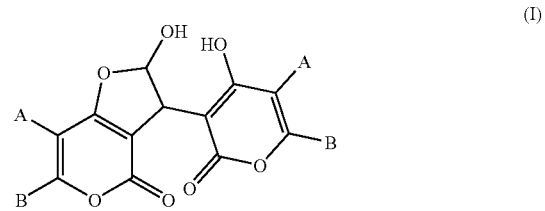

wherein

A and B together with C-atoms to which they are bound represent an aromatic moiety, which may have one, two or more identical or different substituents, which may be halogen, $C_1$–$C_4$-alkyl, $C_2$–$C_4$-alkenyl, $C_2$–$C_4$-alkynyl, halo-$C_1$–$C_4$-alkyil, hydroxy, $C_1$–$C_4$-alkoxy, trifluoromethoxy, $C_1$–$C_4$-alkanoyl, amino, amino-$C_1$–$C_4$-alkyl, N—($C_1$–$C_4$-alkyl)amino, N,N-di($C_1$–$C_4$-alkyl)amino, sulfanyl, $C_1$–$C_4$-alkylsulfanyl, sulfo, $C_1$–$C_4$-alkylsulfo, sulfino, $C_1$–$C_4$-alkilsulfino, carboxy, $C_1$–$C_4$-alkoxycarbonyl, cyano, nitro; or which may be further fused with optionally substituted heteroaromatic moieties or heterocycles.

The objects of the present invention are:
a) compounds of the formula (I),
b) processes and reactive intermediates for their preparation,
c) mixtures of the prepared compounds in amounts sufficent to decrease inflammatory processes or conditions,
d) methods of use of prepared compounds in the treatment of disorders or conditions induced by inflammatory processes.

DETAILED DESCRIPTION OF THE INVENTION

In the context of the present invention the used general terms mainly have the following meanings:

The term "halogen" relates to a halogen atom, which may be fluorine, chlorine, bromine or iodine.

The term "alkyl" relates to alkyl groups having the meaning of alkanes, wherefrom radicals are derived, which may be straight, branched or cyclic or a combination of straight and cyclic ones or of branched and cyclic ones. The preferred straight or branched alkyls are e.g. methyl, ethyl, propyl, iso-propyl, butyl, sec-butyl and tert-butyl. The preferred cyclic alkyls are e.g. cyclopentyl or cyclohexyl. Alkyl may be optionally additionally substituted with one, two, three or more substituents. Such substituents may be a halogen atom (preferably fluorine or chlorine), hydroxy, $C_1$–$C_4$-alkoxy (preferably methoxy or ethoxy), sulfanyl, $C_1$–$C_4$-alkylsulfanyl (preferably methylsulfanyl or ethylsulfanyl), amino, N—($C_1$–$C_4$-alkyl)amino (preferably N-methylamino or N-ethylamino), N,N-di($C_1$–$C_4$-alkyl)amino (preferably dimethylamino or diethylamino), sulfo, $C_1$–$C_4$-alkylsulfo (preferably methylsulfo or ethylsulfo), sulfino, $C_1$–$C_4$-alkilsulfino (preferably methylsulfino).

The term "alkenyl" relates to alkenyl groups having the meaning of hydrocarbon radicals, which may be straight, branched or cyclic or are a combination of straight and cyclic ones or of branched and cyclic ones, but have at least one carbon-carbon double bond. The most frequent alkenyls are ethenyl, propenyl, butenyl or cyclohexenyl. Alkenyl may be optionally additionally substituted with one, two or three halogen atoms. Such substituents may be e.g. 2-chloroethenyl, 1,2-dichloroethenyl or 2-bromopropen-1-yl.

The term "alkynyl" relates to alkynyl groups having the meaning of hydrocarbon radicals, which are straight or branched and contain at least one and at most two carbon-carbon triple bonds. The most frequent alkynyls are e.g. ethynyl, propynyl or butynyl.

The term "alkoxy" relates to straight or branched chains of alkoxy group. Examples of such groups are methoxy, ethoxy, propoxy, prop-2-oxy, butoxy, but-2-oxy or methylprop-2-oxy.

The term "aromatic moiety" relates to the radicals of an aromatic ring e.g. benzene as well as to other fused aromatic rings. The aromatic moiety contains one ring with at least 6 carbon atoms or two rings with totally 10 carbon atoms and alternating double (resonant) bonds between carbon atoms. The most frequently used aromatic moities are e.g. benzene or naphthalene ring. Aromatic groups are linked to A and B sites of the rest of the molecule via any two available adjacent carbon atoms. Under the term aromatic moiety there is also to be understood a benzene ring fused to optionally substituted cycloalkyls, most frequently to cyclohexane.

The term "heteroaromatic moiety" relates to groups having the meaning of aromatic and partially aromatic groups of a monocyclic or bicyclic ring with 4 to 12 atoms, at least one of them being a hetero atom such as O, S or N, wherein two available adjacent carbon atoms are the binding site of the group to the A and B sites of the rest of the molecule. Examples of this type are thiophene, pyrrole, imidazole, pyridine, oxazole, thiazole, pyrazole, tetrazole, pyrimidine, pyrazine, quinoline or triazine rings.

The term "heterocycle" relates to five-member or six-member, completely saturated or partly unsaturated heterocyclic groups containing at least one hetero atom such as O, S or N, wherein two available adjacent carbon atoms are the binding site of the group to the A and B sites of the rest of the molecule. The most frequent examples are morpholinyl, piperidinyl, piperazinyl, pyrrolidinyl, pyrazinyl or imidazolyl.

The term "alkanoyl" group relates to straight chains of acyl group such as formyl, acetyl or propanoyl.

The term "aroyl" group relates to aromatic acyl groups such as benzoyl.

The heteroaromatic moiety or heterocycle may be optionally additionally substituted with one, two or more substituents. The substituents may be halogen (fluorine, chlorine, iodine or bromine), $C_1$–$C_4$ alkyl (preferably methyl, ethyl or isopropyl), trifluoromethyl, cyano, nitro, hydroxy, $C_1$–$C_4$ alkoxy (preferably methoxy or ethoxy), $C_1$–$C_4$ alkyloxycarbonyl (preferably methyloxycarbonyl), sulfanyl, $C_1$–$C_4$ alkylsulfanyl (preferably methylsulfanyl or ethylsulfanyl), amino, N—($C_1$–$C_4$)alkylamino (preferably N-methylamino or N-ethylamino), N,N-di($C_1$–$C_4$-alkyl)-amino (preferably N,N-dimethylamino or N,N-diethylamino), sulfo, $C_1$–$C_4$ alkylsulfo (preferably methylsulfo or ethylsulfo), sulfino, $C_1$–$C_4$ alkylsulfino (preferably methylsulfino).

A further object of the present invention relates to pharmaceutically acceptable salts of the compounds of the formula (I). The compounds representing an object of the present invention comprise at least one acidic hydroxy group on the coumarin nucleus and thus can form salts with pharmaceutically acceptable bases. Examples of such salts formed on hydroxy substituent are e.g. aluminum salts, corresponding salts of alkali metals such as sodium or potassium, salts of earth alkali metals such as calcium or magnesium, pharmaceutically acceptable salts of transient metals such as zinc and copper, salts with ammonia or salts with lower organic amines such as cyclic amines, mono-, di- or trisubstituted lower alkyl amines, further lower hydroxyalkyl amines such as lower mono-, di- or trihydroxyalkyl amines, lower (hydroxyalkyl)alkyl amines or lower polyhydroxyalkyl amines and salts with amino acids. Examples of cyclic amines are morpholine, thiomorpholine, piperidine or pyrrolidine. Suitable lower monoalkylamines are e.g. ethylamine and tert-butylamine, suitable lower dialkyamines are e.g. diethylamine and diisopropylamine, and suitable lower trialkylamines are e.g. trimethylamine and triethylamine. Corresponding lower hydroxylalkyamines are e.g. mono-, di- and triethanolamine, lower (hydroxyalkyl)alkyamines are e.g. N,N-dimethylaminoethanol and N,N-diethylaminoethanol. Amino acids are e.g. lysine, arginine, methylglutamine, alanine or serine. These salts can be prepared in situ during the final isolation and purification of the compounds of the present invention or separately in a reaction with a suitable inorganic or organic base in a manner known to the one skilled in the art.

The prefix "lower" denotes a chain having up to and including seven, especially up to and including four carbon atoms. Lower alkyls are e.g. n-propyl, isopropyl, n-butyl, isobutyl, sec-butyl, tert-butyl, n-pentyl, neopentyl, n-hexyl or n-heptyl, and most frequently ethyl or methyl.

In view of the close connection between free forms and salt forms of the compounds represented by the formula (I), it should be understood that in the present invention the free forms of compounds represented by the formula (I) and their salts are identical forms and in the corresponding context it is suitable to consider the free forms of the compounds of the present invention and their corresponding salts as synonymous.

The present invention also relates to the solvates (most frequently hydrates) that can be formed by the compounds of the formula (I) or their salts.

The compounds represented by the formula (I) and their salts may exist in different physical forms (e.g. in different crystal forms) and the present invention relates to all physical forms (e.g. to all crystal forms) of the compounds represented by the formula (I) and to their mixtures.

The present invention comprises all prodrug forms of the compounds of the formula (I), i.e. compounds, which upon in vivo application in mammals release an active medicinal substance of the formula (I) in the organism. The prodrug forms can be prepared by the modification of any functional group present in a compound of the formula (I) in such a manner that the modified group can be easily desintegrated in vivo while releasing the starting active compound. The hydroxy group is a suitable site for the formation of prodrug forms of such compounds.

The compounds of the present invention may exist in different isomeric forms, which means different tautomeric forms, and they may also can form different geometric isomers or stereoisomers. Isomers, which differ only with regard to the arrangement of the atoms in space arround the asymmetric (chiral) centre, are called "stereoisomers". Two stereoisomers that do not correlate as a subject and its mirror image are called "diastereomers", whereas the ones that correlate as a subject and its mirror image are called "enantiomers". Each enantiomer can be characterised by determining the absolute configuration of the asymmetric centre by the use of Cahn-Ingold-Prelog priority rule and hence characterised as R- or S-isomer. Another way of identification of stereoisomers is the measurement of the rotation of the plane of the polarised light passing through the molecule, namely as a right-rotating (+)-isomer or a left-rotating (−)-isomer. Chiral compounds may exist as single enantiomers or as a mixture of enantiomers. A mixture containing equal proportions of enantiomers is called a "racemic mixture". The present invention relates to all stereoisomers that can be represented by the formula (I), either the ones isolated as single enantiomers or the ones present in a racemic or some other mixture. The methods of determination of stereochemical configuration and separation of stereoisomers are well known from the literature.

The compounds of the formula (I) may also form two or more structural isomers, which are in equilibrium, but may be formed as a consequence of tautomerism. Most frequent are chain isomers, however chain-ring isomers are known as well. Due to the dynamic equilibrium such isomers (tautomers) can easily be transformed from one isomeric form to another. Which of the isomeric forms will prevail in the mixture depends on the kind of compound, on whether the compound is in free form or in the form of any of its salts, on the type of the salt, on the solvent, in which the compound is dissolved, as well as on the pH value of the solution. In the present invention under the term compounds of the formula (I) there should also be understood all tautomeric forms, either chain or cyclic ones, either isolated separately or in a mutual equilibrium mixture of various proportions.

Methods of Preparation

A further object of the present invention relates to a process for the preparation of compounds of the formula (I) and salts thereof comprising a reaction of condensation of the compounds of the formula (II)

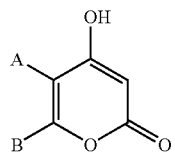

(II)

or of their salts with glyoxal of the formula (III)

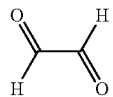

(III)

in an aqueous-organic medium, and/or an optional conversion of the obtained free compounds represented by the formula (I) having such properties that they may also exist in salt forms, into salt forms, and/or an optional conversion of the obtained salts into free compounds or other salts.

The reactions are based on a modified process decribed in EP 0906909, but preferably they are performed in the presence of a solvent inert to the used chemical reagents. Such solvents are aromatic solvents such as toluene, xylene or dipolar aprotic solvents such as aliphatic or cycloaliphatic ethers, dialkyamides of carboxylic acids (e.g. N,N-dimethylformamide) or dimethylsulfoxide. Especially suitable are low-boiling-point solvents miscible with water such as a mixture of acetonitrile and water. In the reactions commercially available glyoxal in the form of a 40% aqueous solution in an equimolar amount or preferably in a considerable excess in proportion to hydroxycoumarin (the most suitable ratio is 2:1) is used. Instead of glyoxal also its derivatives such as 2,3-dihydroxy-1,4-dioxane can be used. The reactions are carried out at temperatures from room temperature to 90° C. (most suitably at the boiling temperature of the reaction mixture). The duration of the reactions is from 1 to 24 hours, which depends on the temperature of the reaction mixture (in the case of acetonitrile and water, 3–6 hours are sufficient). The product is most frequently precipitated by the cooling of the reaction mixture, whereupon it can be slowly separated by sucking off, purified by washing and dried. Other methods of isolation and purification common in preparative organic chemistry can also be used.

Some of the compounds of the formula (II) used in the present invention are commercial products or they are products previously synthesized and described, while others are obtained according to processes described for analogous compounds. Thus e.g. the compounds of the formula (II) can be prepared from the corresponding enamine of the formula (IV)

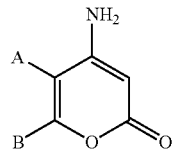

(IV)

in manners understandable per se to one skilled in preparative organic chemistry or known from the literature, e.g. by hydrolysis in a strong acidic medium such as a 50% aqueous solution of sulfuric acid (Desai, N. J. et al., J. Org. Chem. 1957, 22, 388–390) or in a 25% aqueous solution of hydrochloric acid (Sonn, A., Ber. 1917, 50, 1292–1305). Enamine of the formula (IV) can be prepared in a manner well described in the literature, e.g. by the condensation of commercially available phenols with cyanoacetic acid (Sonn, A., Ber. 1917, 50, 1292–1305) or with its alkyl ester such as cyanoacetic acid ethyl ester (Desai, N. J. et al., J. Org. Chem. 1957, 22, 388–390), respectively.

There are also other methods for the preparation of different derivatives of hydroxycoumarin described in much detail, such as a direct method of the action of malonic acid on substituted phenoles (Buckle, D. et al., J. Med. Chem. 1975, 18, 391–394) or more indirect methods starting from substituted o-hydroxyacetophenones (Boyd, J. et al., J. Chem. Soc. 1948, 174–176; Hermodson, M. et al., J. Med. Chem. 1971, 14, 167–169) or hydroxybenzoic acid (Appendino, G. et al., J. Nat. Prod. 1999, 62, 1627–1631; EP 0694257 A1).

In order to avoid undesired participation in chemical reactions it is often necessary to protect, prior to the reaction, certain reactive groups such as some of the hydroxy groups that can be present in hydroxycoumarins, or one of the two aldehyde groups of glyoxal. For this purpose a great number of protecting groups (Green, T. W.; Wuts, P. G. M., Protective Groups in Organic Synthesis, John Wiley and Sons, 1999) can be used. Their selection, use and removal after performed reaction are usual methods in chemical synthesis.

The salts of compounds of formula (I) can be prepared by commonly known processes such as a reaction of compounds of the formula (I) with a corresponding base in a suitable solvent or solvent mixture e.g. ethers (diethylether) or alcohols (ethanol, propanol or isopropanol), or by mixing equivalent amounts of reactants and a subsequent lyophilization and purification of the mixture.

The present invention also relates to reactive intermediates, which are prepared during the preparation of compounds of the formula (I) and of their pharmaceutically acceptable salts. Such intermediates can be isolated and defined or used without isolation in a further phase of chemical synthesis.

A further object of the present invention relates to the use of compounds of the formula (I) and their pharmaceutically acceptable salts in therapeutically effective amounts in the prophylaxis and treatment of diseases and/or conditions resulting from disorders of immunological system, especially inflammatory diseases and conditions (especially asthma) in humans.

A further object of the present invention relates to the use of compounds of the formula (I) and their pharmaceutically acceptable salts as antiinflammatory, antianaphylactic and immunomodulating agents, which—depending on the site of disease—can be differently administered, e.g. per os, parenterally, percutaneously, buccally, rectally or by inhalation in case of local application in respiratory system.

Pharmaceutical Compositions

A further object of the present invention relates to the preparation of pharmaceutical forms of the present compounds formulated in such a manner as to achieve an optimal bioavailability of the active compounds of the formula (I). For percutaneous application the compounds of the formula (I) can be formulated in the form of an ointment, cream, gel or lotion. Ointments, creams and gels can be formulated with a water base or an oil base under the addition of a suitable emulsifier or gelling agent when gel is formulated. The formulation is especially important for the use by inhalation, wherein compounds of the formula (I) can be in the form of aerosol under pressure. For all forms of aerosol formulations there is suggested a micronization of the compounds of the formula (I) being previously homogenized in lactose, glucose, higher fatty acids, sodium salt of dioctylsulfosuccinic acid or most preferably in carboxymethylcellulose, so that the majority of the particles have the size of 5 μm. For the inhalation formulation the aerosol can be mixed with a propellant intended for the spraying of the active substance.

For the inhalation application the compounds of the formula (I) can be used in the form of a dry powder with micronized particles.

Suitable preparations of the compounds of the present invention can be used in the prophylaxis and treatment of several inflammatory diseases and pathological allergical conditions. Examples of such conditions and diseases are, without limitation, asthma, chronic obstructive pulmonary disease, inflammatory nasal diseases such as allergic rhinitis, nasal polyps, dermatological inflammations such as eczemas, psoriasis, allergic dermatitis, neurodermatitis, pruritis, conjunctivitis, rheumatoid arthritis, bowel diseases such as Crohn's disease, colitis and ulcerative colitis, further insulin-dependent diabetes, autoimmune thyroiditis, lupus erythematosus, multiple sclerosis, Raynaud's disease, rheumatoid spondylitis, septic arthritis, polyarthritis, retinitis, inflammatory brain diseases such as meningitis and encephalitis, conditions induced by acute trauma such as brain, miocard and lung lesions, inflammations accompanying infections such as sepsis, glomerulonephritis.

The compounds of the formula (I) can be used individually or in combination with any other commercial product suitable for treating said diseases and/or conditions.

The compounds represented by the formula (I) possess useful pharmacological properties supported by in vitro and in vivo investigations disclosed in the continuation of the present invention.

Biological Assays

Analysis Method of Inhibition of RBL-2H3 Cell Degranulation

RBL-2H3 cell line of rat basophilic leukaemia (ATCC) was used for the investigation of inhibition of degranulation induced by the activation of Fcε receptor type I or calcium ionophors. RBL-2H3 cell line was cultivated in DMEM medium (Invitrogen Corporation) with 10% of phoetal calf serum (Invitrogen Corporation) at 37° C., 5% $CO_2$, 90% relative humidity. Cells were seeded in the same medium into 24-well plates, 50000 per well, and left to reach 80–90% of confluence.

Dilutions of compounds were prepared in DMEM medium without phenol red (Invitrogen Corporation) in concentrations from 200 μM to 1 μM. The medium was removed from the cells and dilutions of compounds were added thereto with the exception of the positive and the negative control where pure DMEM medium was added. Subsequently, to all wells there were added:

1. for the IgE-induced degranulation by Fcε receptor type I, a solution of SPE-1 (dinitrophenyl specific IgE) antibodies (Sigma) and dinitrophenylalbumin (Sigma), both in a final concentration of 0.5 μg/mL,
2. for $Ca^{2+}$-induced degranulation by means of a calcium ionophor, the solution A23187 (Calbiochem) in a final concentration of 250 ng/ml, with the exception of the negative control wells, wherein pure DMEM medium was added. The cells were incubated for one hour at 37° C., 5% $CO_2$, 90% relative humidity. Each dilution as well as the positive and the negative controls were performed in triplicate.

The supernatant (50 μL) was transferred in duplicate to a 96-well plate. Thereto 100 μL of 50 mM sodium citrate buffer with 1 mg/mL para-nitrophenyl-N-acetyl-β-D-glucosaminide (Calbiochem) were added and it was incubated for 1 hour at 37° C. The reaction was stopped with 100 μL of a saturated sodium carbonate solution. The absorbance was measured at 405 nm. The percentage of inhibition was expressed by the formula:

% $inh=(1-(OD_{405}\text{sample}-OD_{405}\text{negative control})/(OD_{405}\text{positive control}-OD_{405}\text{negative control}))*100$.

The majority of the compounds inhibited the degranulation of RBL-2H3 cells, but most active were the compounds 6, 7, 12, 15, 17, 34, 36, 38, 40 demonstrating an action in doses from 100–3 μM. Ketotifen as a standard inhibits degranulation in concentrations from 200–50 μM Hyperreactivity of the Bronchi The hyperreactivity of the bronchi was measured by pletismometric method (Buxco pletismometer), which is based on pressure difference and was performed in conscious and non-bound animals. The action of the compounds on the hyperreactivity of the bronchi induced by methacholine (Sigma) in aerosol form in different concentrations was expressed by the percentage of the increase of the enhanced pause value (PENH) above the base line, which was recorded without a cholinergic stimulant.

Compound 6 was used i.p. in mice in a dose of 10 mg/kg within a period beginning two days prior to provocative test to the end of the test, totally for 4 days. The hyperreactivity of the bronchi was measured by pletismometric method over 24 hours after the provocative test. Compound 6 statistically significantly (t-test, p<0.05) decreased the hyperreactivity of respiratory airways in relation to the positive control group at methacholine concentration of 25 mg/mL.

Compound 36 was used i.p. in rats in a dosis of 10 mg/kg within a period beginning two days prior to the provocative test to the end of test, totally for 4 days. The hyperreactivity of the bronchi was measured by pletismometric method over 24 hours after the provocative test. The compound statistically significantly (t-test, p<0.01) decreased the hyperreactivity of respiratory airways in relation to the positive control group at methacholine concentration of 50 mg/mL.

EXAMPLES

The present invention is illustrated by the following Examples, which are given only as illustrative examples and do not limit the scope of the invention in any way. The preparation processes were mostly carried at atmospheric pressure and at room temperature. In each example the final product was characterised by means of one or several of the following methods: high-performance liquid chromatography (HPLC) and/or high-performance liquid chromatography connected to a mass spectrometer (HPLC-MS) and spectroscopy of nuclear magnetic resonance (NMR). Temperatures were expressed in Celsius degrees and the reaction time in hours: DMSO=dimethylsulfoxide, THF=tetrahydrofurane, LDA=lithium diisopropylamide, DMF=N,N-dimethylformamide.

Compound 1: 2-Hydroxy-3-(4-hydroxy-2-oxo-2H-chromen-3-yl)-2,3-dihydro-4H-furo[3,2-c]chromene-4-one

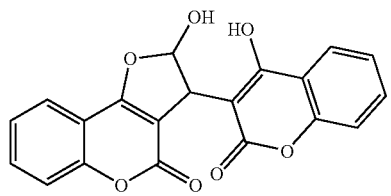

Example 1

4-Hydroxycoumarin (Aldrich) (810 mg, 5.0 mmole) was mixed with a 40% aqueous solution of glyoxal (Aldrich) (575 µL; 5.0 mmole). Acetonitrile (10 mL) was added thereto and the reaction mixture was refluxed for 6 hours. By cooling the solution to room temperature a white precipitate was precipitated, which was filtered and washed with acetonitrile. There were obtained 670 mg (73.6%) of compound 1, which did not need additional purification.

$^1$H-NMR (300 MHz, DMSO-$d_6$) δ/ppm: 4.84 (s, 1H); 6.29 (bs, 1H); 7.28–7.58 (m, 4H); 7.63–7.80 (m, 3H); 8.04 (d, J=7.6 Hz, 1H), 12.02 (bs, 1H); MS m/z: ES$^-$ (acetonitrile:water) [M-H]$^-$: 363.2.

Compound 2: 2-Hydroxy-3-(4-hydroxy-5-methyl-2-oxo-2H-chromen-3-yl)-9-methyl-2,3-dihydro-4H-furo[3,2-c]chromene-4-one

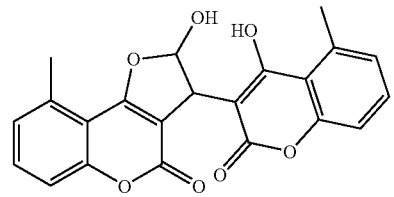

Example 2

4-Hydroxy-5-methylcoumarin (100 mg; 0.57 mmole) was mixed with a 40% aqueous solution of glyoxal (130 µL; 1.1 mmole). Acetonitrile (6 mL) was added thereto and the reaction mixture was refluxed for 9 hours. By cooling the solution to room temperature a white precipitate was precipitated, which was filtered and washed with acetonitrile. There were obtained 33.5 mg (29%) of compound 2 which did not need additional purification.

$^1$H-NMR (300 MHz, DMSO-$d_6$) δ/ppm: 2.71 (s, 3H); 2.76 (s, 3H); 4.83 (d, J=3.8 Hz, 1H); 6.29 (d, J=3.5 Hz, 1H); 7.15–7.20 (m, 2H); 7.26 (d, J=8.4 Hz, 1H); 7.47 (dd, J=8.0 Hz, J=8.0 Hz, 1H); 7.53 (dd, J=8.0 Hz, J=8.0 Hz, 1H); 8.26 (bs, 1H); 11.7 (bs, 1H); $^{13}$C-NMR (75.4 MHz, DMSO-$d_6$) δ/ppm: 20.7; 23.4; 42.8; 101.5; 102.0; 108.6; 111.4; 114.5; 114.5; 115.0; 126.4; 127.6; 131.3; 131.9; 135.7; 137.3; 153.4; 155.3; 158.2; 160.7; 164.7; 166.2; MS m/z: ES$^-$ (acetonitrile:water) [M-H]$^-$: 392.8.

Compound 3: 2-Hydroxy-3-(4-hydroxy-6-methyl-2-oxo-2H-chromen-3-yl)-8-methyl-2,3-dihydro-4H-furo[3,2-c]chromene-4-one

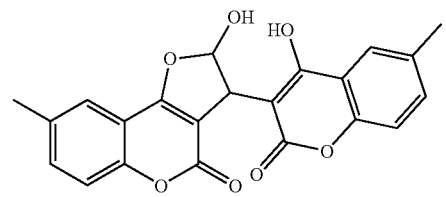

Example 3

4-Hydroxy-6-methylcoumarin (88 mg; 0.5 mmole) was mixed with a 40% aqueous solution of glyoxal (288 µL; 2.5 mmole). Acetonitrile (3 mL) was added thereto and the reaction mixture was refluxed for 3 hours. By cooling the solution to room temperature a white precipitate was precipitated, which was filtered and washed with acetonitrile. There were obtained 84 mg (86%) of compound 3, which did not need additional purification.

$^1$H-NMR (300 MHz, DMSO-$d_6$) δ/ppm: 2.38 (s, 3H); 2.41 (s, 3H); 4.78 (s, 1H); 6.26 (s, 1H); 7.28 (d, J=8.5 Hz, 1H); 7.35 (d, J=8.2 Hz, 1H); 7.45–7.52 (m, 2H); 7.55 (bs, 1H); 7.82 (bs, 1H); 8.20 (bs, 1H); 11.90 (bs, 1H); MS m/z: ES$^-$ (acetonitrile:water) [M-H]$^-$: 391.1.

Compound 4: 2-Hydroxy-3-(4-hydroxy-7-methyl-2-oxo-2H-chromene-3-yl)-7-methyl-2,3-dihydro-4H-furo[3,2-c]chromene-4-one

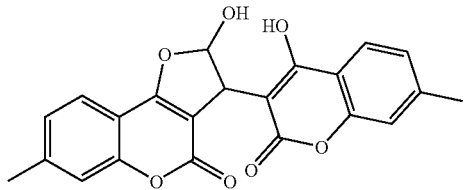

Example 4

4-Hydroxy-7-methylcoumarin (88 mg, 0.5 mmole) was mixed with a 40% aqueous solution of glyoxal (288 μL; 2.5 mmole). Acetonitrile (10 mL) was added thereto and the reaction mixture was refluxed for 3 hours. By cooling the solution to room temperature a white precipitate was precipitated, which was filtered and washed with acetonitrile. There were obtained 46 mg (47%) of compound 4, which did not need additional purification.

$^1$H-NMR (300 MHz, DMSO-$d_6$) δ/ppm: 2.41 (s, 3H); 2.44 (s, 3H); 4.76 (bs, 1H); 6.25 (bs, 1H); 7.11–7.29 (m, 4H); 7.64 (d, J=7.7 Hz, 1H); 7.91 (d, J=7.7 Hz, 1H); 8.20 (bs, 1H); 11.80 (bs, 1H); $^{13}$C-NMR (75.4 MHz, DMSO-$d_6$) δ/ppm: 21.0; 21.2; 43.7; 100.7; 100.9; 109.4; 109.6; 113.3; 116.3; 116.6; 122.3; 123.1; 125.0; 125.3; 143.1; 143.5; 152.2; 154.6; 158.5; 161.6; 162.0; 165.0; MS m/z: ES$^-$ (acetonitrile:water) [M-H]$^-$: 391.0.

Compound 5: 2-Hydroxy-3-(4-hydroxy-8-methyl-2-oxo-2H-chromene-3-yl)-6-methyl-2,3-dihydro-4H-furo[3,2-c]chromene-4-one

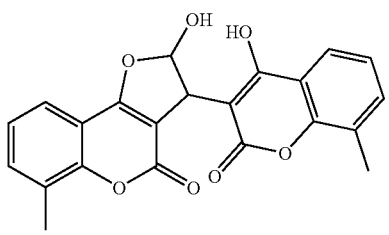

Example 5

4-Hydroxy-8-methylcoumarin (88 mg, 0.5 mmole) was mixed with a 40% aqueous solution of glyoxal (288 μL; 2.5 mmole). Acetonitrile (3 mL) was added thereto and the reaction mixture was refluxed for 3 hours. By cooling the solution to room temperature a white precipitate was precipitated, which was filtered and washed with acetonitrile. There were obtained 80 mg (81%) of compound 5, which did not need additional purification.

$^1$H-NMR (300 MHz, DMSO-$d_6$) δ/ppm: 2.34 (s, 3H); 2.37 (s, 3H); 4.80 (bs, 1H); 6.28 (bs, 1H); 7.26–7.35 (m, 2H); 7.51–7.62 (m, 3H); 7.86 (d, J=7.7 Hz, 1H); 8.28 (bs, 1H); 11.99 (bs, 1H); MS m/z: ES$^-$ (acetonitrile:water) [M-H]$^-$: 391.1.

Compound 6: 2-Hydroxy-3-(4-hydroxy-5,7-dimethyl-2-oxo-2H-chromene-3-yl)-7,9-dimethyl-2,3-dihydro-4H-furo[3,2-c]chromene-4-one

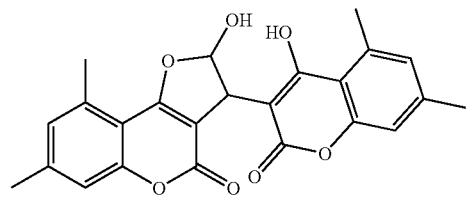

Example 6

4-Hydroxy-5,7-dimethylcoumarin (190 mg; 1.0 mmole) was mixed with a 40% aqueous solution of glyoxal (288 μL; 2.5 mmole). Acetonitrile (10 mL) was added thereto and the reaction mixture was refluxed for 2.5 hours. By cooling the solution to room temperature a beige precipitate was precipitated, which was filtered and washed with acetonitrile. There were obtained 150 mg (71%) of compound 6, which did not need additional purification.

$^1$H-NMR (300 MHz, DMSO-$d_6$) δ/ppm: 2.28 (s, 3H); 2.33 (s, 3H); 2.65 (s, 3H); 2.71 (s, 3H); 4.78 (d, J=3.8 Hz, 1H); 6.25 (d, J=3.6 Hz, 1H); 7.01 (s, 1H); 7.03 (s, 1H); 7.09 (s, 1H); 7.16 (s, 1H); MS m/z: ES$^+$ (acetonitrile:water) [MH]$^+$: 420.8.

Compound 7: 2-Hydroxy-3-(4-hydroxy-5,8-dimethyl-2-oxo-2H-chromene-3-yl)-6,9-dimethyl-2,3-dihydro-4H-furo[3,2-c]chromene-4-one

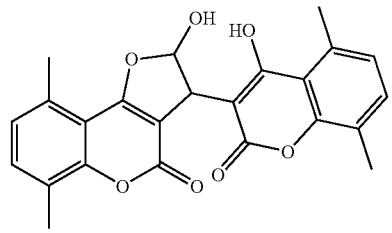

Example 7

4-Hydroxy-5,8-dimethylcoumarin (190 mg; 1.0 mmole) was mixed with a 40% aqueous solution of glyoxal (288 μL; 2.5 mmole). Acetonitrile (5 mL) was added thereto and the reaction mixture was refluxed for 2.5 hours. The reaction mixture was evaporated and the obtained crude product was recrystallized from a mixture of acetone:water (1:1), whereat 132 mg (63%) of white crystalline compound 7 were obtained.

$^1$H-NMR (300 MHz, DMSO-$d_6$) δ/ppm: 2.26 (s, 3H); 2.31 (s, 3H); 2.66 (s, 3H); 2.72 (s, 3H); 4.84 (d, J=3.5 Hz, 1H); 6.28 (d, J=3.1 Hz, 1H); 7.05 (d, J=7.8 Hz, 1H); 7.9 (d, J=7.9 Hz, 1H); 7.35 (d, J=7.6 Hz, 1H); 7.42 (d, J=7.6 Hz, 1H); 8.24 (bs, 1H); 12.00 (bs, 1H); MS m/z: ES$^+$ (acetonitrile:water) [MH]$^+$: 420.8.

Compound 8: 2-Hydroxy-3-(4-hydroxy-6,7-dimethyl-2-oxo-2H-chromene-3-yl)-7,8-dimethyl-2,3-dihydro-4H-furo[3,2-c]chromene-4-one

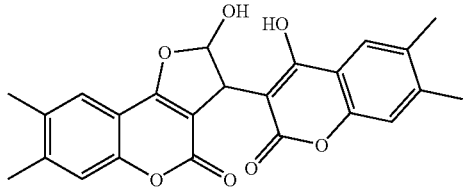

Example 8

4-Hydroxy-6,7-dimethylcoumarin (Aldrich) (190 mg; 1.0 mmole) was mixed with a 40% aqueous solution of glyoxal (288 μL; 2.5 mmole). Acetonitrile (10 mL) was added thereto and the reaction mixture was refluxed for 4 hours. By cooling the solution to room temperature a white precipitate was precipitated, which was filtered and washed with acetonitrile. There were obtained 182 mg (86%) of compound 8, which did not need additional purification.

$^1$H-NMR (300 MHz, DMSO-$d_6$) δ/ppm: 2.28 (s, 3H); 2.32 (s, 6H); 2.34 (s, 3H); 4.75 (d, J=3.3 Hz, 1H); 6.23 (d, 1H); 7.20 (s, 1H); 7.27 (s, 1H); 7.51 (s, 1H); 7.77 (s, 1H); 8.97 (bs, 1H); 11.87 (bs, 1H); $^{13}$C-NMR (75.4 MHz, DMSO-$d_6$) δ/ppm: 18.6; 18.9; 19.5; 19.8; 43.7; 100.7; 100.9; 109.3; 109.6; 113.3; 116.6; 116.9; 122.3; 123.2; 132.3; 132.9; 142.0; 142.4; 150.5; 153.0; 158.6; 161.6; 161.9; 164.9; MS m/z: ES$^-$ (acetonitrile:water) [M-H]$^-$: 419.4.

Compound 9: 2-Hydroxy-3-(4-hydroxy-7,8-dimethyl-2-oxo-2H-chromene-3-yl)-6,7-dimethyl-2,3-dihydro-4H-furo[3,2-c]chromene-4-one

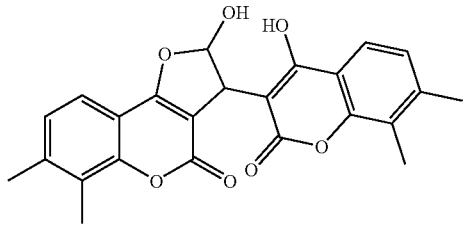

Example 9

4-Hydroxy-7,8-dimethylcoumarin (95 mg; 0.5 mmole) was mixed with a 40% aqueous solution of glyoxal (144 μL; 1.25 mmole). Acetonitrile (10 mL) was added thereto and the reaction mixture was refluxed for 3 hours. By cooling the solution to room temperature a white precipitate was precipitated, which was filtered and washed with acetonitrile. There were obtained 85 mg (80%) of compound 9 which did not need additional purification.

$^1$H-NMR (300 MHz, DMSO-$d_6$) δ/ppm: 2.25 (s, 3H); 2.28 (s, 3H); 2.35 (s, 3H); 2.39 (s, 3H); 4.77 (d, J=3.1 Hz, 1H); 6.26 (d, J=3.5 Hz, 1H); 7.19 (d, J=8.3 Hz, 1H); 7.22 (d, J=8.2 Hz, 1H); 7.50 (d, J=8.0 Hz, 1H); 7.75 (d, J=8.1 Hz, 1H); MS m/z: ES$^+$ (acetonitrile:water) [MH]$^+$: 421.2.

Compound 10: 2-Hydroxy-3-(4-hydroxy-6,8-dimethyl-2-oxo-2H-chromene-3-yl)-6,8-dimethyl-2,3-dihydro-4H-furo[3,2-c]chromene-4-one

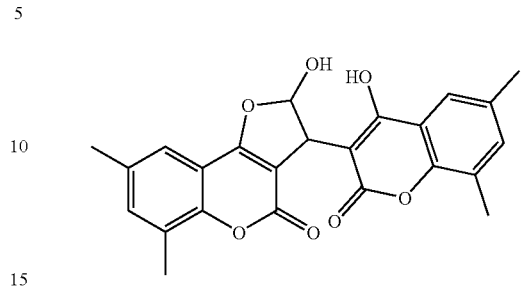

Example 10

4-Hydroxy-6,8-dimethylcoumarin (190 mg; 1.0 mmole) was mixed with a 40% aqueous solution of glyoxal (288 μL; 2.5 mmole). Acetonitrile (5 mL) was added thereto and the reaction mixture was refluxed for 2 hours. By cooling the solution to room temperature a white precipitate was precipitated, which was filtered and washed with acetonitrile. There were obtained 156 mg (74%) of compound 10 which did not need additional purification.

$^1$H-NMR (300 MHz, DMSO-$d_6$) δ/ppm: 2.30 (s, 3H); 2.32 (s, 3H); 2.34 (s, 3H); 2.37 (s, 3H); 4.79 (d, J=3.5 Hz, 1H); 6.26 (d, J=3.6 Hz, 1H); 7.34 (s, 1H); 7.39 (s, 2H); 7.65 (s, 1H); 11.85 (bs, 1H); MS m/z: ES$^+$ (acetonitrile:water) [MH]$^+$: 420.8.

Compound 11: 8-Ethyl-3-(6-ethyl-4-hydroxy-2-oxo-2H-chromene-3-yl)-2-hydroxy-2,3-dihydro-4H-furo[3,2-c]chromene-4-one

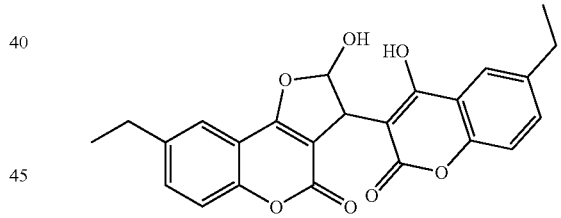

Example 11

6-Ethyl-4-hydroxycoumarin (95 mg; 0.5 mmole) was mixed with a 40% aqueous solution of glyoxal (288 μL; 2.5 mmole). Acetonitrile (2 mL) was added thereto and the reaction mixture was refluxed for 3 hours. By cooling the solution to room temperature a white precipitate was precipitated, which was filtered and washed with acetonitrile. There were obtained 57 mg (54.2%) of compound 11, which did not need additional purification.

$^1$H-NMR (300 MHz, DMSO-$d_6$) δ/ppm: 1.22 (m, 6H); 2.71 (m, 4H); 4.80 (d, J=3.4 Hz, 1H); 6.28 (d, J=3.5 Hz, 1H); 7.31 (d, J=8.4 Hz, 1H); 7.38 (d, J=8.3 Hz, 1H); 7.50 (d, J=8.0 Hz, 1H); 7.55 (d, J=8.0 Hz, 1H); 7.57 (s, 1H); 7.87 (s, 1H); $^{13}$C-NMR (75.4 MHz, DMSO-$d_6$) δ/ppm: 15.5; 15.6; 27.3; 27.6; 43.9; 101.4; 101.8; 109.4; 111.9; 115.5; 116.2; 116.5; 120.9; 121.9; 132.1; 132.5; 139.5; 140.0; 150.4; 152.8; 158.5; 161.5; 161.9; 164.9; MS m/z: ES$^+$ (acetonitrile:water) [MH]$^+$: 420.9.

Compound 12: 6-Ethyl-3-(8-ethyl-4-hydroxy-2-oxo-2H-chromene-3-yl)-2-hydroxy-2,3-dihydro-4H-furo[3,2-c]chromene-4-one

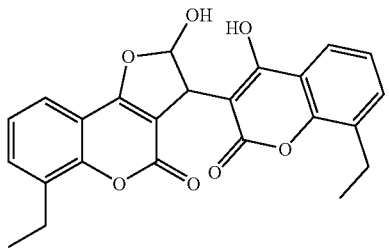

Example 12

8-Ethyl-4-hydroxycoumarin (95 mg; 0.5 mmole) was mixed with a 40% aqueous solution of glyoxal (288 μL; 2.5 mmole). Acetonitrile (2 mL) was added thereto and the reaction mixture was refluxed for 3 hours. By cooling the solution to room temperature a white precipitate was precipitated, which was filtered and washed with acetonitrile. There were obtained 64 mg (61%) of compound 12, which did not need additional purification.

$^1$H-NMR (300 MHz, DMSO-d$_6$) δ/ppm: 1.21 (m, 6H); 2.78 (m, 4H); 4.82 (d, J=3.2 Hz, 1H); 6.30 (d, J=3.5 Hz, 1H); 7.32 (t, J=7.8 Hz, 1H); 7.36 (t, J=7.6 Hz, 1H); 7.53 (d, J=7.3 Hz, 1H); 7.58(d, J=7.8, 1H); 7.62 (d, J=7.8 Hz, 1H); 7.87 (d, J=7.8 Hz, 1H); 11.80 (bs, 1H); $^{13}$C-NMR (75.4 MHz, DMSO-d$_6$) δ/ppm: 14.0 (2C); 22.0; 22.3; 43.8; 101.3; 101.7; 109.4; 111.9; 115.7; 120.4; 121.1; 123.5; 124.0; 131.0; 131.4; 131.8; 132.1; 149.9; 152.3; 158.3; 161.3; 162.2; 165.3; MS m/z: ES$^+$ (acetonitrile:water) [MH]$^+$: 420.8.

Compound 13: 2-Hydroxy-3-(4-hydroxy-6-isopropyl-2-oxo-2H-chromene-3-yl)-8-isopropyl-2,3-dihydro-4H-furo[3,2-c]chromene-4-one

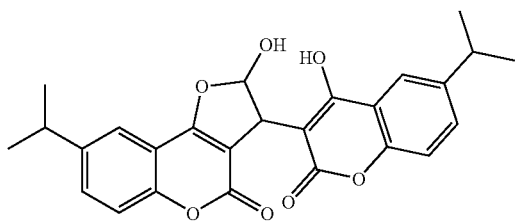

Example 13

4-Hydroxy-6-isopropylcoumarin (102 mg; 0.5 mmole) was mixed with a 40% aqueous solution of glyoxal (230 μL; 2.0 mmole). Acetonitrile (1 mL) was added thereto and the reaction mixture was refluxed for 5 hours. By cooling the solution to room temperature a white precipitate was precipitated, which was filtered and washed with acetonitrile. There were obtained 34 mg (30%) of compound 13, which did not need additional purification.

$^1$H-NMR (300 MHz, DMSO-d$_6$) δ/ppm: 1.23 (d, J=7.2 Hz, 6H); 1.26 (d, J=7.4 Hz, 6H); 3.00 (m, 2H); 4.79 (d, J=2.4 Hz, 1H); 6.28 (d, J=3.3 Hz, 1H); 7.31 (d, J=8.4 Hz, 1H); 7.38 (d, J=8.5 Hz, 1H); 7.57 (m, 3H); 7.92 (s, 1H); 12.00 (bs, 1H); $^{13}$C-NMR (75.4 MHz, DMSO-d$_6$) δ/ppm: 23.8 (4C); 32.7; 33.0; 43.9; 101.5; 101.8; 109.4; 111.8; 115.5; 116.2; 116.6; 119.4; 120.4; 130.9; 131.2; 144.2; 144.5; 150.4; 152.8; 158.5; 161.6; 162.0; 164.9; MS m/z: ES$^-$ (acetonitrile:water) [M-H]$^-$: 447.0.

Compound 14: 2-Hydroxy-3-(4-hydroxy-8-isopropyl-2-oxo-2H-chromene-3-yl)-6-isopropyl-2,3-dihydro-4H-furo[3,2-c]chromene-4-one

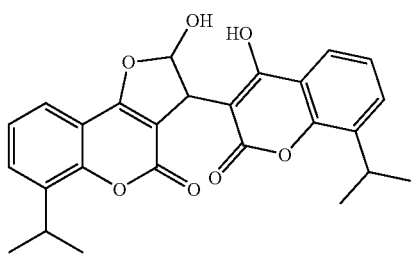

Example 14

4-Hydroxy-8-isopropylcoumarin (102 mg; 0.5 mmole) was mixed with a 40% aqueous solution of glyoxal (288 μL; 2.5 mmole). Acetonitrile (1.5 mL) was added thereto and the reaction mixture was refluxed for 5 hours. By cooling the solution to room temperature a white precipitate was precipitated, which was filtered and washed with acetonitrile. There were obtained 18 mg (16%) of compound 14, which did not need additional purification.

$^1$H-NMR (300 MHz, DMSO-d$_6$) δ/ppm: 1.25 (m, 12H); 3.44 (m, 2H); 4.82 (d, J=3.0 Hz, 1H); 6.30 (d, J=3.4 Hz, 1H); 7.35 (dd, J=7.9 Hz, J=7.8 Hz, 1H); 7.39 (dd, J=7.8 Hz, J=7.5 Hz, 1H); 7.61 (m, 3H); 12.00 (bs, 1H); $^{13}$C-NMR (75.4 MHz, DMSO-d$_6$) δ/ppm: 22.3 (2C); 22.4 (2C); 26.2; 26.4; 43.8; 101.3; 101.6; 109.4; 111.9; 115.7; 120.3; 121.0; 123.7 124.1; 129.2; 129.5; 135.6; 135.8; 149.3; 151.7; 158.2; 159.4; 162.2; 165.4; MS m/z: ES$^+$ (acetonitrile:water) [MH]$^+$: 448.9.

Compound 15: 2-Hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one

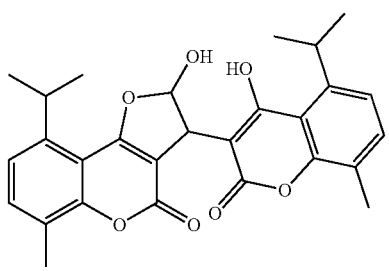

Example 15

4-Hydroxy-5-isopropyl-8-methylcoumarin (109 mg; 0.5 mmole) was mixed with a 40% aqueous solution of glyoxal (288 μL; 2.5 mmole). Acetonitrile (2 mL) was added thereto and the reaction mixture was refluxed for 3 hours. By cooling the solution to room temperature a white precipitate was precipitated, which was filtered and washed with acetonitrile. There were obtained 22 mg (18.5%) of compound 15, which did not need additional purification.

$^1$H-NMR (300 MHz, DMSO-$d_6$) δ/ppm: 1.25 (d, J=6.9 Hz, 6H); 1.28 (d, J=6.8 Hz, 6H); 2.27 (s, 3H); 2.32 (s, 3H); 4.08 (sept, J=6.8 Hz, 1H); 4.39 (sept, J=6.7 Hz, 1H), 4.86 (d, J=3.4 Hz, 1H); 6.30 (d, J=3.2 Hz, 1H); 7.25 (d, J=7.9 Hz, 2H); 7.43 (d, J=7.9 Hz, 1H); 7.49 (d, J=7.9 Hz, 1H); $^{13}$C-NMR (75.4 MHz, DMSO-$d_6$) δ/ppm: 15.3; 15.6; 23.4; 24.3; 28.8; 29.1; 42.6; 100.8; 102.2; 108.2; 110.2; 113.6; 120.5; 121.4; 122.6; 123.1; 132.5; 133.1; 144.4; 146.0; 151.3; 153.4; 158.1; 160.4; 164.8; 166.3; MS m/z: ES$^+$ (acetonitrile:water) [MH]$^+$: 476.9.

Compound 16: 2-Hydroxy-3-(4-hydroxy-6,8-diisopropyl-2-oxo-2H-chromene-3-yl)-6,8-diisopropyl-2,3-dihydro-4H-furo[3,2-c]chromene-4-one

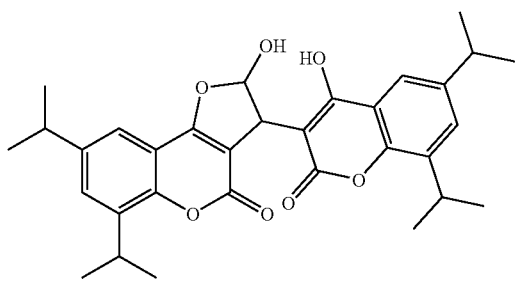

Example 16

4-Hydroxy-6,8-diisopropylcoumarin (86 mg; 0.35 mmole) was mixed with a 40% aqueous solution of glyoxal (200 μL; 1.05 mmole). Acetonitrile (3 mL) was added thereto and the reaction mixture was refluxed for 3 hours. The reaction mixture was diluted with ethyl acetate and extracted with water. The organic layer was dried with sodium sulfate and evaporated under reduced pressure. After the purification of the yellow oily residue (12 g) on a silica gel column in a solvent system chloroform:acetone:acetic acid (60:20:1), 35 mg (38%) of white powdery compound 16 were obtained.

MS m/z: ES$^+$ (acetonitrile:water) [MH]$^+$: 533.1.

Compound 17: 2-Hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one

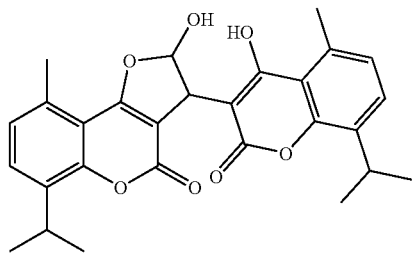

Example 17

4-Hydroxy-8-isopropyl-5-methylcoumarin (109 mg; 0.5 mmole) was mixed with a 40% aqueous solution of glyoxal (230 μL; 2.0 mmole). Acetonitrile (2 mL) was added thereto and the reaction mixture was refluxed for 6 hours. Compound 17 (10.5 mg; 8.8%) was obtained from the reaction mixture by extraction on a solid carrier (Supelco, Supelclean LC-18. 1 g).

$^1$H-NMR (300 MHz, DMSO-$d_6$) δ/ppm: 1.22 (m, 12H); 2.67 (s, 3H); 2.73 (s, 3H); 3.39 (m, 2H); 4.83 (d, J=3.6 Hz, 1H); 6.28 (bs, 1H); 7.12 (d, J=7.7 Hz, 1H); 7.16 (d, J=7.9 Hz, 1H); 7.40 (d, J=7.8 Hz, 1H); 7.47 (d, J=7.9 Hz, 1H); about 12.0 (bs, 1H); MS m/z: ES$^+$ (acetonitrile:water) [MH]$^+$: 477.1.

Compound 18: 2-Hydroxy-3-(4-hydroxy-5-methoxy-2-oxo-2H-chromene-3-yl)-9-methoxy-2,3-dihydro-4H-furo[3,2-c]chromene-4-one

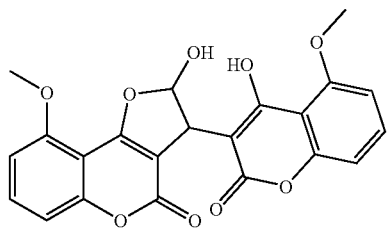

Example 18

4-Hydroxy-5-methoxycoumarin (96 mg; 0.5 mmole) was mixed with a 40% aqueous solution of glyoxal (288 μL; 2.5 mmole). Acetonitrile (5 mL) was added thereto and the reaction mixture was refluxed for 1 hour. By cooling the solution to room temperature a white precipitate was precipitated, which was filtered and washed with acetonitrile. There were obtained 63 mg (59%) of compound 18, which did not need additional purification.

$^1$H-NMR (300 MHz, DMSO-$d_6$) δ/ppm: 3.92 (s, 3H); 4.01 (s, 3H); 4.59 (d, J=4.0 Hz, 1H); 6.18 (bs, 1H); 6.97–7.04 (m, 4H); 7.60 (m, 2H); 8.18 (d, J=7.3 Hz, 1H); 10.36 (bs, 1H); $^{13}$C-NMR (75.4 MHz, DMSO-$d_6$) δ/ppm: 42.0; 56.2; 56.9; 100.5; 101.0; 102.8; 104.0; 106.3; 106.5;

108.7; 108.9; 109.5; 133.0; 153.0; 155.9; 156.1; 156.2; 158.1; 162.2; 165.1; MS m/z: ES⁻ (acetonitrile:water) [M-H]⁻: 423.0

Compound 19: 2-Hydroxy-3-(4-hydroxy-6-methoxy-2-oxo-2H-chromene-3-yl)-8-methoxy-2,3-dihydro-4H-furo[3,2-c]chromene-4-one

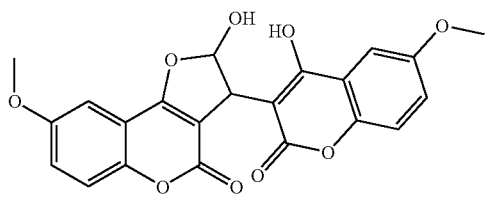

Example 19

4-Hydroxy-6-methoxycoumarin (96 mg; 0.5 mmole) was mixed with a 40% aqueous solution of glyoxal (288 μL; 2.5 mmole). Acetonitrile (5 mL) was added thereto and the reaction mixture was refluxed for 4 hours. By cooling the solution to room temperature a white precipitate was precipitated, which was filtered and washed with acetonitrile. There were obtained 74 mg (70%) of compound 19, which did not need additional purification.

¹H-NMR (300 MHz, DMSO-$d_6$) δ/ppm: 3.86 (3H, s); 3.81 (3H, s); 4.49 (1H, bs); 6.27 (1H, m); 7.15–7.54 (6H, m); 11.80 (bs, 1H); ¹³C-NMR (75.4 MHz, DMSO-$d_6$) δ/ppm: 44.0; 55.6 (2H); 101.8; 102.2; 104.1; 105.7; 109.4; 112.4; 116.2; 117.5; 118.0; 119.9; 120.7; 146.4; 148.9; 155.3; 155.4; 158.4; 161.6; 161.7; 164.6; MS m/z: ES⁻ (acetonitrile:water) [M-H]⁻: 423.0.

Compound 20: 2-Hydroxy-3-(4-hydroxy-7-methoxy-2-oxo-2H-chromene-3-yl)-7-methoxy-2,3-dihydro-4H-furo[3,2-c]chromene-4-one

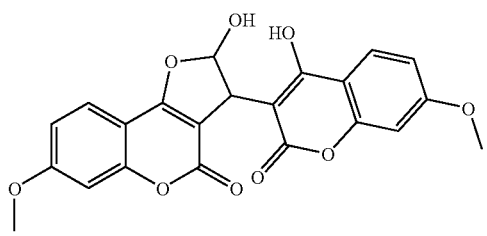

Example 20

4-Hydroxy-7-methoxycoumarin (96 mg; 0.5 mmole) was mixed with a 40% aqueous solution of glyoxal (288 μL; 2.5 mmole). Acetonitrile (5 mL) was added thereto and the reaction mixture was refluxed for 2 hours. By cooling the solution to room temperature a white precipitate was precipitated, which was filtered and washed with acetonitrile. There were obtained 80 mg (75%) of compound 20, which did not need additional purification.

¹H-NMR (300 MHz, DMSO-$d_6$) δ/ppm: 3.86 (s, 6H); 4.71 (bs, 1H); 6.22 (bs, 1H); 6.87–7.05 (m, 4H); 7.67 (d, J=8.6 Hz, 1H); 7.92 (d, J=8.8 Hz, 1H); 11.89 (bs, 1H); MS m/z: ES⁻ (acetonitrile:water) [M-H]⁻: 423.0.

Compound 21: 2-Hydroxy-3-(4-hydroxy-8-methoxy-2-oxo-2H-chromene-3-yl)-6-methoxy-2,3-dihydro-4H-furo[3,2-c]chromene-4-one

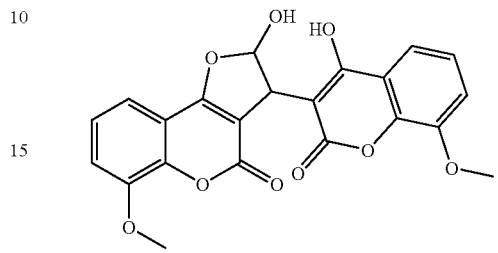

Example 21

4-Hydroxy-8-methoxycoumarin (96 mg; 0.5 mmole) was mixed with a 40% aqueous solution of glyoxal (288 μL; 2.5 mmole). Acetonitrile (5 mL) was added thereto and the reaction mixture was refluxed for 45 minutes. By cooling the solution to room temperature a white precipitate was precipitated, which was filtered and washed with acetonitrile. There were obtained 95 mg (90%) of compound 21, which did not need additional purification.

¹H-NMR (300 MHz, DMSO-$d_6$) δ/ppm: 3.84 (s, 3H); 3.87 (s, 3H); 4.71 (d, J=3.2 Hz, 1H); 6.22 (d, J=3.2 Hz, 1H); 6.86–7.05 (m, 4H); 7.66 (d, J=8.7 Hz, 1H); 7.92 (d, J=9.9 Hz, 1H); 11.89 (bs, 1H); ¹³C-NMR (75.4 MHz, DMSO-$d_6$) δ/ppm: 43.5; 55.8 (2C); 99.0; 100.4; 100.8; 105.3; 109.0; 109.4; 111.9; 112.3; 123.7; 124.6; 154.0; 156.4; 158.6; 161.7; 162.2; 162.5; 162.9; 165.2; MS m/z: ES⁻ (acetonitrile:water) [M-H]⁻: 423.3.

Compound 22: 2-Hydroxy-3-(4-hydroxy-5,7-dimethoxy-2-oxo-2H-chromene-3-yl)-7,9-dimethoxy-2,3-dihydro-4H-furo[3,2-c]chromene-4-one

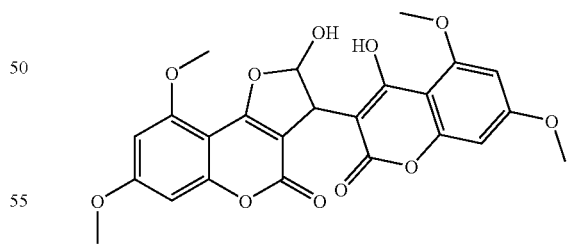

Example 22

4-Hydroxy-5,7-dimethoxycoumarin (111 mg; 0.5 mmole) was mixed with a 40% aqueous solution of glyoxal (288 μL; 2.5 mmole). Acetonitrile (5 mL) was added thereto and the reaction mixture was refluxed for 2 hours. After cooling the reaction mixture to room temperature the solvent was evaporated under reduced pressure and the crude residue was recrystallized from the solvent mixture of acetone:water, whereat there were obtained 90 mg (74%) of compound 22.

¹H-NMR (300 MHz, DMSO-d₆) δ/ppm: 3.85 (s, 3H); 3.85 (s, 3H); 3.88 (s, 3H); 3.97 (s, 3H); 4.51 (d, J=4.0 Hz, 1H); 6.12 (m, 1H); 6.52 (d, J=2.2 Hz, 1H); 6.57 (d, J=2.2 Hz, 1H); 6.61 (d, J=2.2 Hz, 1H); 6.63 (d, J=2.2 Hz, 1H); 8.08 (d, J=2.2 Hz, 1H); 10.2 (bs, 1H); ¹³C-NMR (75.4 MHz, DMSO-d₆) δ/ppm: 42.1; 55.9; 56.0; 56.2; 56.9; 93.4; 93.8; 95.0; 95.3; 96.8; 97.8; 98.2; 98.2; 108.7; 154.8; 157.2; 157.3; 157.6; 158.2; 162.4; 163.1; 163.4; 165.4; MS m/z: ES+⁻ (acetonitrile:water) [MH]⁺: 484.7.

Compound 23: 2-Hydroxy-3-(4-hydroxy-6,7-dimethoxy-2-oxo-2H-chromene-3-yl)-7,8-dimethoxy-2,3-dihydro-4H-furo[3,2-c]chromene-4-one

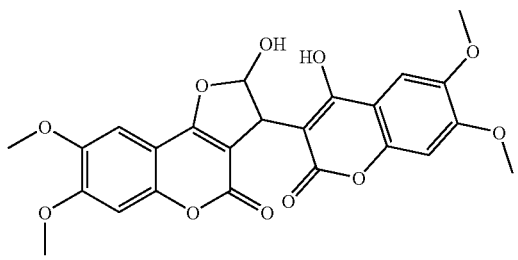

Example 23

4-Hydroxy-6,7-dimethoxycoumarin (111 mg; 0.5 mmole) was mixed with a 40% aqueous solution of glyoxal (288 μL; 2.5 mmole). Acetonitrile (5 mL) was added thereto and the reaction mixture was refluxed for 2 hours. By cooling the solution to room temperature a white precipitate was precipitated, which was filtered and washed with acetonitrile. There were obtained 60 mg (50%) of compound 23, which did not need additional purification.

¹H-NMR (300 MHz, DMSO-d₆) δ/ppm: 3.81 (s, 3H); 3.86 (s, 3H); 3.87 (s, 6H); 4.72 (d, J=3.0 Hz, 1H); 6.22 (d, J=3.3 Hz, 1H); 6.96 (s, 1H); 7.05 (s, 1H); 7.10 (s, 1H); 7.52 (s, 1H); 11.7 (bs, 1H); ¹³C-NMR (75.4 MHz, DMSO-d₆) δ/ppm: 42.6; 54.6; 54.8; 55.0; 98.3; 98.8; 95.0; 99.3; 101.6; 102.8; 103.1; 106.5; 108.3; 144.5; 144.8; 146.9; 149.5; 151.5; 152.0; 157.7; 161.1; 164.1; MS m/z: ES+⁻ (acetonitrile:water) [MH]⁺: 484.8.

Compound 24: 3-(4,5-Dihydroxy-2-oxo-2H-chromene-3-yl)-2,9-dihydroxy-2,3-dihydro-4H-furo[3,2-c]chromene-4-one

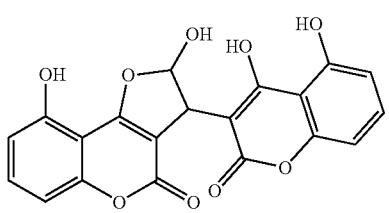

Example 24

4,5-Dihydroxycoumarin (100 mg; 0.56 mmole) was mixed with a 40% aqueous solution of glyoxal (299 μL; 2.8 mmole). Acetonitrile (5 mL) was added and the reaction mixture was stirred at room temperature overnight. The obtained white precipitate was filtered and washed with acetonitrile. There were obtained 40 mg (36%) of compound 24, which did not need additional purification.

¹H-NMR (300 MHz, DMSO-d₆) &ppm: 4.55 (bs, 1H); 6.15 (bs, 1H); 6.75–6.82 (m, 4H); 7.38–7.43 (m, 2H); 10.89 (bs, 1H); ¹³C-NMR (75.4 MHz, DMSO-d₆) δ/ppm: 42.8; 98.6; 101.1; 102.3; 104.0; 106.8; 107.3; 109.1; 109.4; 110.1; 132.5 (2C); 153.1; 154.9; 155.3; 155.9; 158.3; 160.3; 164.7; 165.5; MS m/z: ES⁺ (acetonitrile:water) [MH]⁺: 396.8.

Compound 25: 3-(4,6-Dihydroxy-2-oxo-2H-chromene-3-yl)-2,8-dihydroxy-2,3-dihydro-4H-furo[3,2-c]chromene-4-one

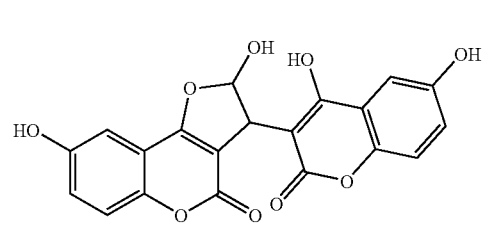

Example 25

4,6-Dihydroxycoumarin (178 mg; 1.0 mmole) was mixed with a 40% aqueous solution of glyoxal (288 μL; 2.5 mmole). Acetonitrile (10 mL) was added thereto and the reaction mixture was refluxed for 3 hours. By cooling the solution to room temperature a white precipitate was precipitated, which was filtered and washed with acetonitrile. There were obtained 154 mg (78%) of compound 25, which did not need additional purification.

¹H-NMR (300 MHz, DMSO-d₆) δ/ppm: 4.76 (bs, 1H); 6.23 (d, J=3.0 Hz, 1H); 7.01–7.33 (m, 6H); 9.90 (bs, 1H); 11.85 (bs, 2H); 12.39 (bs, 1H); MS m/z: ES⁺ (acetonitrile:water) [MH]⁺: 396.7.

Compound 26: 3-(4,7-Dihydroxy-2-oxo-2H-chromene-3-yl)-2,7-dihydroxy-2,3-dihydro-4H-furo[3,2-c]chromene-4-one

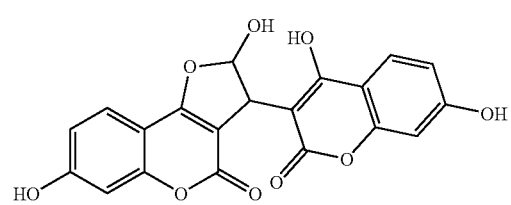

Example 26

4,7-Dihydroxycoumarin (178 mg; 1.0 mmole) was mixed with a 40% aqueous solution of glyoxal (288 μL; 2.5 mmole). Acetonitrile (10 mL) was added thereto and the reaction mixture was refluxed for 1 hour. By cooling the solution to room temperature a white precipitate was precipitated, which was filtered and washed with acetonitrile. There were obtained 170 mg (86%) of compound 26, which did not need additional purification.

$^1$H-NMR (300 MHz, DMSO-$d_6$) δ/ppm: 4.67 (d, J=3.2 Hz, 1H); 6.18 (d, J=2.9 Hz, 1H); 6.68 (s, 1H); 6.75 (s, 1H); 6.81–6.91 (m, 2H); 7.58 (d, J=8.6 Hz, 1H); 7.83 (d, J=8.7 Hz, 1H); 10.58 (bs, 1H); 10.64 (bs, 1H); 11.73 (bs, 1H); MS m/z: ES$^-$ (acetonitrile:water) [M-H]$^-$: 395.

Compound 27: 3-(4,7-Dihydroxy-8-methyl-2-oxo-2H-chromene-3-yl)-2,7dihydroxy-6-methyl-2,3-dihydro-4H-furo[3,2-c]chromene-4-one

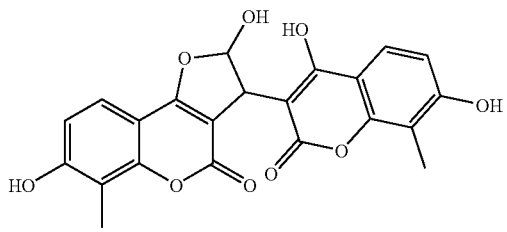

Example 27

4,7-Dihydroxy-8-methylcoumarin (96 mg; 0.5 mmole) was mixed with a 40% aqueous solution of glyoxal (288 μL; 2.5 mmole). Acetonitrile (5 mL) was added thereto and the reaction mixture was refluxed for 3 hours. By cooling the solution to room temperature a white precipitate was precipitated, which was filtered and washed with acetonitrile. There were obtained 58 mg (50%) of compound 27, which did not need additional purification.

$^1$H-NMR (300 MHz, DMSO-$d_6$) δ/ppm: 2.13 (s, 3H); 2.15 (s, 3H); 4.70 (d, J=3.5 Hz, 1H); 6.19 (d, J=3.6 Hz, 1H); 6.87 (d, J=8.8 Hz, 1H); 6.91 (d, J=8.5 Hz, 1H); 7.44 (d, J=8.6 Hz, 1H); 7.69 (d, J=8.8 Hz, 1H); 10.40 (bs, 1H); 10.51 (bs, 1H); 11.59 (bs, 1H); $^{13}$C-NMR (75.4 MHz, DMSO-$d_6$) δ/ppm: 7.94; 8.17; 43.5; 98.1; 98.2; 104.1; 107.8; 109.3; 110.4; 111.0; 111.4; 111.8; 120.5; 121.3; 151.9; 154.4; 158.8; 158.9; 159.3; 162.0; 162.6; 165.7; MS m/z: ES$^+$ (acetonitrile:water) [MH]$^+$: 424.8.

Compound 28: 3-(4,7-Dihydroxy-5-methyl-2-oxo-2H-chromene-3-yl)-2,7-dihydroxy-9-methyl-2,3-dihydro-4H-furo[3,2-c]chromene-4-one

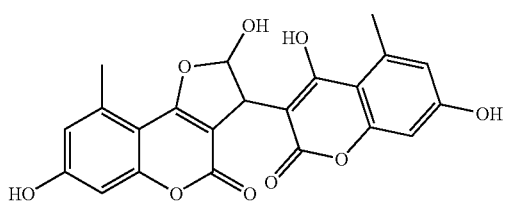

Example 28

4,7-Dihydroxy-5-methylcoumarin (200 mg; 1.04 mmole) was mixed with a 40% aqueous solution of glyoxal (597 μL; 13 mmole). Acetonitrile (5 mL) was added thereto and the reaction mixture was refluxed for 8 hours. By cooling the solution to room temperature a white precipitate was precipitated, which was filtered and washed with acetonitrile. There were obtained 175 mg (79%) of compound 28, which did not need additional purification.

$^1$H-NMR (300 MHz, DMSO-$d_6$) δ/ppm: 2.61 (s, 3H); 2.156 (s, 3H); 4.69 (d, J=3.9 Hz, 1H); 6.20 (d, J=3.8 Hz, 1H); 6.49 (d, J=2.2 Hz, 1H); 6.58 (m, 2H); 6.63 (s, 1H); 8.00 (bs, 1H); 10.41 (bs, 1H); 11.50 (bs, 1H); $^{13}$C-NMR (75.4 MHz, DMSO-$d_6$) δ/ppm: 19.8; 22.5; 41.4; 96.4; 97.4; 98.9; 99.3; 102.6; 106.2; 107.4; 113.9; 115.0; 136.1; 137.8; 154.3; 156.4; 157.5; 158.8; 159.6; 160.0; 164.0; 165.7; MS m/z: ES$^+$ (acetonitrile:water) [MH]$^+$: 424.8.

Compound 29: 2,6,7-Trihydroxy-3-(4,7,8-trihydroxy-2-oxo-2H-chromene-3-yl)-2,3-dihydro-4H-furo[3,2-c]chromene-4-one

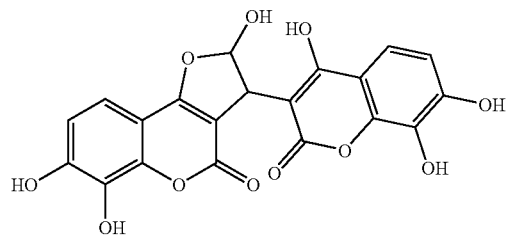

Example 29

4,7,8-Trihydroxycoumarin (97 mg; 0.5 mmole) was mixed with a 40% aqueous solution of glyoxal (288 μL; 2.5 mmole). Acetonitrile (10 mL) was added thereto and the reaction mixture was refluxed for 3 hours. The solvent was evaporated under reduced pressure and the obtained oily precipitate was triturated with cold water. The separated precipitate was filtered and washed with water, whereat there were obtained 50 mg (46%) of yellow compound 29.

$^1$H-NMR (300 MHz, DMSO-$d_6$) δ/ppm: 4.89 (d, J=3.7 Hz, 1H); 6.18 (d, J=3.4 Hz, 1H); 6.80 (d, J=8.7 Hz, 1H); 6.85 (d, J=8.6 Hz, 1H); 7.07 (d, J=8.6 Hz, 1H); 7.35 (d, J=8.7 Hz, 1H); 9.32 (bs, 2H); 10.10 (bs, 2H); 11.59 (bs, 1H); MS m/z: ES$^+$ (acetonitrile:water) [MH]$^+$: 428.9.

Compound 30: 9-Fluoro-3-(5-fluoro-4-hydroxy-2-oxo-2H-chromene-3-yl)-2-hydroxy-2,3-dihydro-4H-furo[3,2-c]chromene-4-one

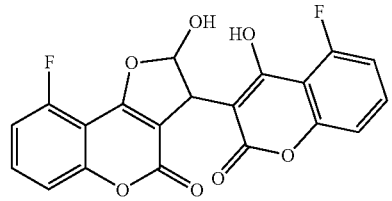

Example 30

5-Fluoro-4-hydroxycoumarin (53 mg; 0.3 mmole) was mixed with a 40% aqueous solution of glyoxal (173 µL; 1.5 mmole). Acetonitrile (2.5 mL) was added thereto and the reaction mixture was refluxed for 4 hours. By cooling the solution to room temperature a white precipitate was precipitated, which was filtered and washed with acetonitrile. There were obtained 23 mg (38%) of compound 30, which did not need additional purification.

$^1$H-NMR (300 MHz, DMSO-$d_6$) δ/ppm: 4.80 (bs, 1H); 5.25 (bs, 1H, aldehyde form); 6.30 (d, J=2.3 Hz, 1H); 6.96–7.34 (m, 4H); 7.56–7.75 (m, 2H); 8.30 (bs, 1H); 9.15 (bs, 1H, aldehyde form); MS m/z: ES$^+$ (acetonitrile:water) [MH]$^+$: 400.8.

Compound 31: 8-Fluoro-3-(6-fluoro-4-hydroxy-2-oxo-2H-chromene-3-yl)-2-hydroxy-2,3-dihydro-4H-furo[3,2-c]chromene-4-one

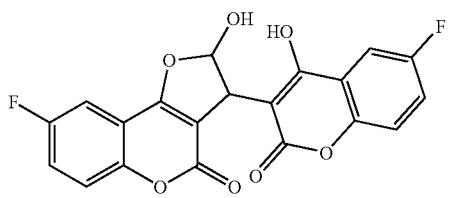

Example 31

6-Fluoro-4-hydroxycoumarin (180 mg; 1.0 mmole) was mixed with a 40% aqueous solution of glyoxal (574 µL; 5.0 mmole). Acetonitrile (8 mL) was added thereto and the reaction mixture was refluxed for 6 hours. By cooling the solution to room temperature a white precipitate was precipitated, which was filtered and washed with acetonitrile. There were obtained 62 mg (31%) of compound 31, which did not need additional purification.

$^1$H-NMR (300 MHz, DMSO-$d_6$) δ/ppm: 4.85 (bs, 1H); 6.35 (bs, 1H); 7.40–7.84 (m, 6H); 9.36 (bs, 1H); $^{13}$C-NMR (75.4 MHz, DMSO-$d_6$) δ/ppm: 42.8; 101.0; 101.6; 107.1 (d, J=24.8 Hz); 108.1 (d, J=25.7 Hz); 108.6; 111.9(d); 115.9(d); 117.4(d); 117.8(d); 118.7 (d, J=23.0 Hz); 119.0 (d, J=20 Hz); 147.4; 149.7; 156.7(d, 241 Hz); 158.1 (d, 236 Hz); 160.2; 162.2; 163.1; 165.4; MS m/z: ES$^-$ (acetonitrile:water) [M-H]$^-$: 399.0.

Compound 32: 2-Hydroxy-3-(4-hydroxy-6-chloro-2-oxo-2H-chromene-3-yl)-8-chloro-2,3-dihydro-4H-furo[3,2-c]chromene-4-one

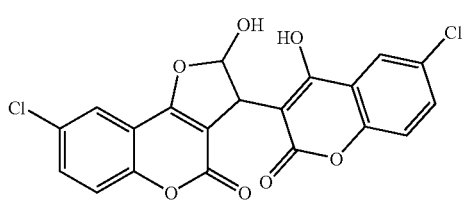

Example 32

4-Hydroxy-6-chlorocoumarin (98 mg; 0.5 mmole) was mixed with a 40% aqueous solution of glyoxal (288 µL; 2.5 mmole). Acetonitrile (5 mL) was added thereto and the reaction mixture was refluxed for 4 hours. By cooling the solution to room temperature a white precipitate was precipitated, which was filtered and washed with acetonitrile. There were obtained 31.8 mg (29%) of compound 32, which did not need additional purification.

$^1$H-NMR (300 MHz, DMSO-$d_6$) δ/ppm: 4.81 (bs, 1H); 6.31 (bs, 1H); 7.33–7.77 (m, 5H); 8.06 (s, 1H), 9.31 (bs, 1H); MS m/z: ES$^-$ (acetonitrile:water) [M-H]$^-$: 431.2; 433.2; 435.2.

Compound 33: 8-Bromo-3-(6-bromo-4-hydroxy-2-oxo-2H-chromene-3-yl)-2-hydroxy-2,3-dihydro-4H-furo[3,2-c]chromene-4-one

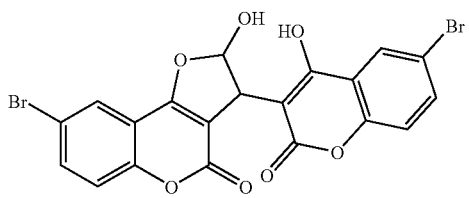

Example 33

6-Bromo-4-hydroxycoumarin (120 mg; 0.5 mmole) was mixed with a 40% aqueous solution of glyoxal (288 µL; 2.5 mmole). Acetonitrile (5 mL) was added thereto and the reaction mixture was refluxed for 4 hours. By cooling the solution to room temperature a white precipitate was precipitated, which was filtered and washed with acetonitrile. There were obtained 20 mg (24%) of compound 33, which did not need additional purification.

$^1$H-NMR (300 MHz, DMSO-$d_6$) δ/ppm: 4.82 (bs, 1H); 5.34 (bs, 1H, aldehyde form); 6.33 (bs, 1H); 7.25–7.40 (m, 2H); 7.72–7.88 (m, 3H); 8.19 (bs, 1H); 9.26 (bs, 1H, aldehyde form); $^{13}$C-NMR (75.4 MHz, DMSO-$d_6$) δ/ppm: 42.7; 101.1; 101.6; 108.6; 112.7; 114.7; 115.0; 116.7; 117.6; 117.9; 122.9; 124.2; 133.8; 134.2; 149.7; 152.3; 156.7; 160.0; 162.6; 164.9; MS m/z: ES$^-$ (acetonitrile:water) [M-H]$^-$: 518.6, 520.6; 522.6.

Compound 34: 2-Hydroxy-3-(4-hydroxy-6-iodo-2-oxo-2H-chromene-3-yl)-8-iodo-2,3-dihydro-4H-furo[3,2-c]chromene-4-one

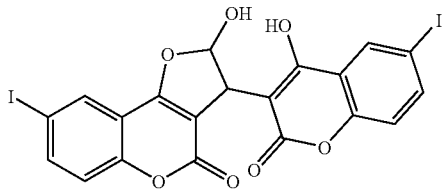

Example 34

4-Hydroxy-6-iodocoumarin (200 mg; 0.7 mmole) was mixed with a 40% aqueous solution of glyoxal (401 µL; 3.5 mmole). Acetonitrile (5 mL) was added thereto and the reaction mixture was refluxed for 3 hours. By cooling the solution to room temperature a white precipitate was precipitated, which was filtered and washed with acetonitrile. There were obtained 70 mg (32%) of compound 34, which did not need additional purification.

$^1$H-NMR (300 MHz, DMSO-$d_6$) δ/ppm: 4.78 (bs, 1H); 6.28 (bs, 1H); 6.91–7.31 (m, 2H); 7.70–8.16 (m, 4H); 9.33 (bs, 1H); MS m/z: ES$^+$ (acetonitrile:water) [MH]$^+$: 617.2.

Compound 35: 7-Fluoro-3-(7-fluoro-4-hydroxy-2-oxo-2H-chromene-3-yl)-2-hydroxy-2,3-dihydro-4H-furo[3,2-c]chromene-4-one

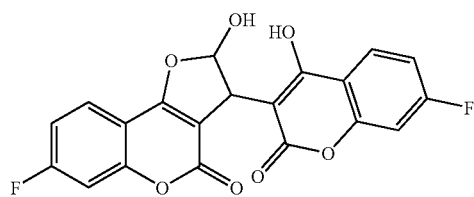

Example 35

7-Fluoro-4-hydroxycoumarin (140 mg; 0.77 mmole) was mixed with a 40% aqueous solution of glyoxal (442 μL; 3.85 mmole). Acetonitrile (5 mL) was added thereto and the reaction mixture was refluxed for 5 hours. By cooling the solution to room temperature a white precipitate was precipitated, which was filtered and washed with acetonitrile. There were obtained 66 mg (42%) of compound 35, which did not need additional purification.

$^1$H-NMR (300 MHz, DMSO-$d_6$) δ/ppm: 4.57 (bs, 1H); 6.69 (bs, 1H); 7.15–7.17 (m, 6H); 8.20 (bs, 1H); MS m/z: ES$^-$ (acetonitrile:water) [M-H]$^-$: 399.3.

Compound 36: 2-Hydroxy-3-(4-hydroxy-7-chloro-2-oxo-2H-chromene-3-yl)-7-chloro-2,3-dihydro-4H-furo[3,2-c]chromene-4-one

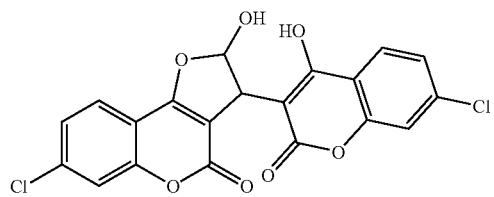

Example 36

4-Hydroxy-7-chlorocoumarin (196 mg; 1.0 mmole) was mixed with a 40% aqueous solution of glyoxal (574 μL; 5.0 mmole). Acetonitrile (8 mL) was added thereto and the reaction mixture was refluxed for 4 hours. By cooling the solution to room temperature a white precipitate was precipitated, which was filtered and washed with acetonitrile. There were obtained 145 mg (67%) of compound 36, which did not need additional purification.

$^1$H-NMR (300 MHz, DMSO-$d_6$) δ/ppm: 4.79 (bs, 1H); 6.30 (bs, 1H); 7.32–8.13 (m, 6H); 9.30 (bs, 1H); MS m/z: ES$^-$ (acetonitrile:water) [M-H]$^-$: 430.8; 432.8; 434.7.

Compound 37: 2-Hydroxy-3-(4-hydroxy-8-chloro-2-oxo-2H-chromene-3-yl)-6-chloro-2,3-dihydro-4H-furo[3,2-c]chromene-4-one

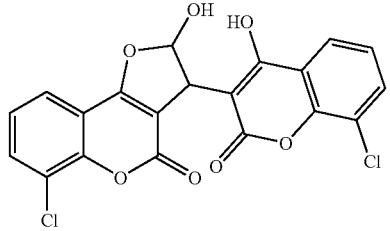

Example 37

4-Hydroxy-8-chlorocoumarin (98 mg; 0.5 mmole) was mixed with a 40% aqueous solution of glyoxal (288 μL; 2.5 mmole). Acetonitrile (5 mL) was added thereto and the reaction mixture was refluxed for 5 hours. By cooling the solution to room temperature a white precipitate was precipitated, which was filtered and washed with acetonitrile. There were obtained 53 mg (49%) of compound 37, which did not need additional purification.

$^1$H-NMR (300 MHz, DMSO-$d_6$) δ/ppm: 4.85 (bs, 1H); 5.34 (bs, 1H, aldehyde form); 6.42 (bs, 1H); 7.28–7.48 (m, 2H); 7.72–7.89 (m, 3H); 7.99 (d, J=7.9 Hz, 1H); 9.25 (bs, 1H, aldehyde form): $^{13}$C-NMR (75.4 MHz, DMSO-$d_6$) δ/ppm: 43.8; 101.7; 102.2; 109.8; 113.6; 117.6; 119.9; 120.2; 121.8; 122.6; 124.4; 125.5; 132.3; 132.8; 147.6; 149.8; 157.2; 160.5; 161.8; 164.7 MS m/z: ES$^-$ (acetonitrile:water) [M-H]$^-$: 430.9; 432.8; 435.1.

Compound 38: 2-Hydroxy-3-(4-hydroxy-6-chloro-7-methyl-2-oxo-2H-chromene-3-yl)-8-chloro-7-methyl-2,3-dihydro-4H-furo[3,2-c]chromene-4-one

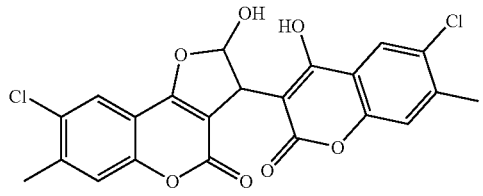

Example 38

4-Hydroxy-6-chloro-7-methylcoumarin (210 mg; 1.0 mmole) was mixed with a 40% aqueous solution of glyoxal (288 μL; 2.5 mmole). Acetonitrile (4 mL) was added thereto and the reaction mixture was refluxed for 3 hours. By cooling the solution to room temperature a white precipitate was precipitated, which was filtered and washed with acetonitrile. There were obtained 31.8 mg (29%) of compound 38, which did not need additional purification.

$^1$H-NMR (300 MHz, DMSO-$d_6$) δ/ppm: 4.79 (bs, 1H); 6.29 (bs, 1H); 7.45 (s, 1H); 7.53 (s, 1H); 7.74 (s, 1H); 8.05 (s, 1H), 8.98 (bs, 1H); $^{13}$C-NMR (75.4 MHz, DMSO-$d_6$) δ/ppm: 19.7; 20.1; 43.8; 101.4; 101.9; 109.6; 111.2; 115.2; 118.6; 119.0; 121.8; 123.0; 128.6; 128.9; 140.5; 140.9;

150.9; 152.9; 158.0; 161.0; 163.9; MS m/z: ES+ (acetonitrile:water) [MH]+: 460.7, 462.7, 464.6.

Compound 39: 2-Hydroxy-3-(1-hydroxy-3-oxo-3H-benzo[f]chromen-2-yl)-2,3-dihydro-4H-benzo[f]furo[3,2-c]chromene-4-one

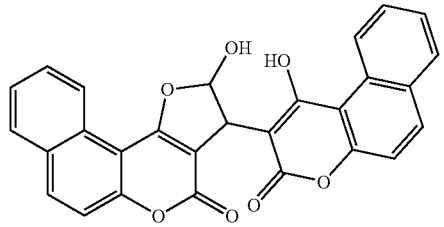

Example 39

1-Hydroxy-3H-benzo[f]chromene-3-one (150 mg; 0.7 mmole) was mixed with a 40% aqueous solution of glyoxal (401 μL; 3.5 mmole). Acetonitrile (5 mL) was added thereto and the reaction mixture was refluxed for 4.5 hours. By cooling the solution to room temperature a white precipitate was precipitated, which was filtered and washed with acetonitrile. There were obtained 135 mg (82%) of compound 39, which did not need additional purification.

$^1$H-NMR (300 MHz, DMSO-d$_6$) δ/ppm: 5.06 (bs, 1H); 6.52 (bs, 1H); 7.51–7.80 (m, 6H), 8.06–8.28 (m, 4H); 9.03 (d, J=8.5 Hz, 1H); 9.44 (d, J=8.4 Hz), 1H); MS m/z: ES+ (acetonitrile:water) [MH]+: 465.4.

Compound 40: 2-Hydroxy-3-(4-hydroxy-2-oxo-2H-benzo[g]chromen-3-yl)-2,3-dihydro-4H-benzo[g]furo[3,2-c]chromene-4-one

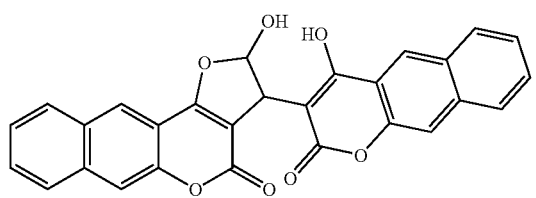

Example 40

4-Hydroxy-2H-benzo[g]chromene-2-one (150 mg; 0.7 mmole) was mixed with a 40% aqueous solution of glyoxal (401 μL; 3.5 mmole). Acetonitrile (5 mL) was added thereto and the reaction mixture was refluxed for 4.5 hours. By cooling the solution to room temperature a white precipitate was precipitated, which was filtered and washed with acetonitrile. There were obtained 130 mg (79%) of compound 40, which did not need additional purification.

$^1$H-NMR (300 MHz, DMSO-d$_6$) δ/ppm: 4.94 (bs, 1H); 6.40 (bs, 1H); 7.56–7.67 (m, 4H); 7.78-(s, 1H); 7.90–8.09 (m, 4H); 8.20 (d, J=7.4 Hz, 1H); 8.47 (s, 1H); 8.67 (s, 1H); 12.2 (bs, 1H); MS m/z: ES+ (acetonitrile:water) [MH]+: 465.2.

Compound 41: 2-Hydroxy-1-(4-hydroxy-2-oxo-2H-benzo[h]chromen-3-yl)-1,2-dihydro-11H-benzo[h]furo[3,2-c]chromene-11-one

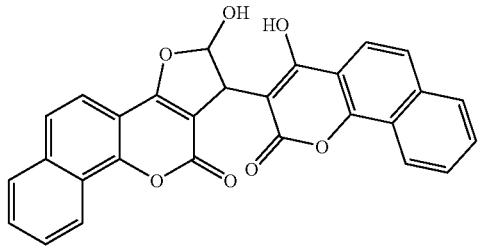

Example 41

4-Hydroxy-2H-benzo[h]chromene-2-one (42.4 mg; 0.2 mmole) was mixed with a 40% aqueous solution of glyoxal (115 μL; 1.0 mmole). Acetonitrile (5 mL) was added thereto and the reaction mixture was refluxed for 2 hours. By cooling the solution to room temperature a white precipitate was precipitated, which was filtered and washed with acetonitrile. There were obtained 39 mg (84%) of compound 41, which did not need additional purification.

$^1$H-NMR (300 MHz, DMSO-d$_6$) δ/ppm: 4.94 (bs, 1H); 6.43 (bs, 1H); 7.45–7.81 (m, 4H); 7.91–7.96 (m, 2H); 8.04–8.11 (m, 3H); 8.36 (m, 3H); MS m/z: ES− (acetonitrile:water) [M-H]−: 463.

Compound 42: 2-Hydroxy-3-(4-hydroxy-7-methoxy-2-oxo-2H-benzo[g]chromen-2-yl)-9-methoxy-2,3-dihydro-4H-benzo[g]furo[3,2-c]chromene-4-one

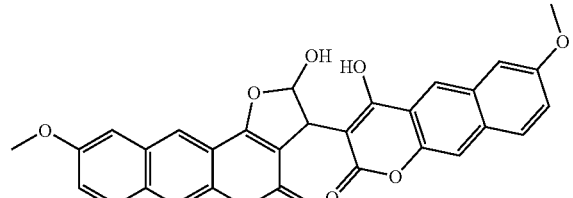

Example 42

4-Hydroxy-7-methoxy-2H-benzo[h]chromene-2-one (121 mg; 0.5 mmole) was mixed with a 40% aqueous solution of glyoxal (288 μL; 2.5 mmole). Acetonitrile (5 mL) was added thereto and the reaction mixture was refluxed for 4 hours. By cooling the solution to room temperature a yellow precipitate was precipitated, which was filtered and washed with acetonitrile. There were obtained 95 mg (72%) of compound 42, which did not need additional purification.

$^1$H-NMR (300 MHz, DMSO-d$_6$) δ/ppm: 3.91 (s, 6H); 4.91 (bs, 1H); 6.37 (bs, 1H); 7.03–8.62 (10H, m, Ar); MS m/z: ES+ (acetonitrile) [MH]+ 525.3.

Compound 43: 2-Hydroxy-3-(4-hydroxy-9-methoxy-2-oxo-2H-benzo[g]chromene-2-yl)-7-methoxy-2,3-dihydro-4H-benzo [g]furo[3,2-c]chromene-4-one

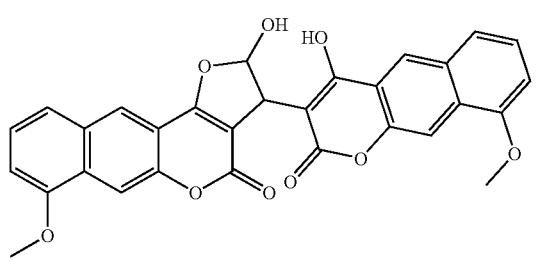

Example 43

4-Hydroxy-9-methoxy-2H-benzo[g]chromene-2-one (121 mg; 0.5 mmole) was mixed with a 40% aqueous solution of glyoxal (288 µL; 2.5 mmole). Acetonitrile (5 mL) was added thereto and the reaction mixture was refluxed for 2 hours. By cooling the solution to room temperature a yellow precipitate was precipitated, which was filtered and washed with acetonitrile. There were obtained 108 mg (82%) of compound 43, which did not need additional purification.

$^1$H-NMR (300 MHz, DMSO-$d_6$) δ/ppm: 4.00 (s, 6H); 4.93 (bs, 1H); 6.39 (bs, 1H); 7.10 (m, 2H); 7.47 (m, 2H); 7.62 (d, J=7.7 Hz, 1H); 7.75 (d, J=5.5 Hz, 1H) 7.89 (s, 1H); 7.99 (s, 1H); 8.42 (s, 1H), 8.61 (s, 1H); MS m/z: ES$^+$ (water:acetonitrile) [MH]$^+$ 525.1.

Compound 44: 3-(4,9-Dihydroxy-2-oxo-2H-benzo[g]chromene-2-yl)-2,7-dihydroxy-2,3-dihydro-4H-benzo[g]furo[3,2-c]chromene-4-one

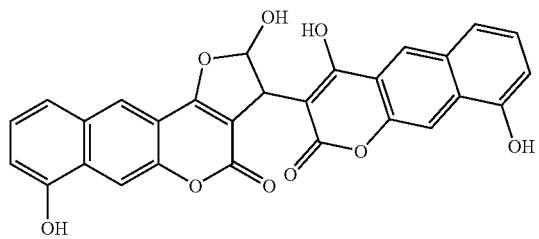

Example 44

4,9-Dihydroxy-2H-benzo[g]chromene-2-one (114 mg; 0.5 mmole) was mixed with a 40% aqueous solution of glyoxal (288 µL; 2.5 mmole). Acetonitrile (3 mL) was added thereto and the reaction mixture was refluxed for 2 hours. By cooling the solution to room temperature a yellow precipitate was precipitated, which was filtered and washed with acetonitrile. There were obtained 78 mg (63%) of compound 44, which did not need additional purification.

$^1$H-NMR (300 MHz, DMSO-$d_6$) δ/ppm: 4.92 (1H, bs); 6.39 (1H, bs); 6.91–8.57 (10H, m); 10.45 (3H, bs); MS m/z: ES$^-$ (water:acetonitrile) [M-H]$^-$ 495.1.

Compound 45: 3-(4,7-Dihydroxy-2-oxo-2H-benzo[g]chromene-2-yl)-2,9-dihydroxy-2,3-dihydro-4H-benzo[g]furo[3,2-c]chromene-4-one

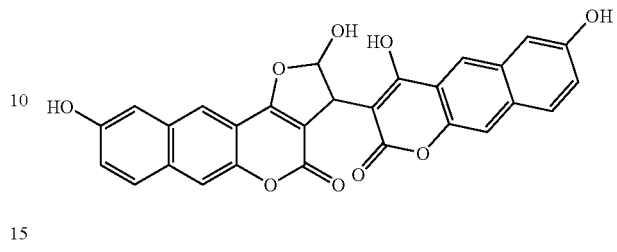

Example 45

4,7-Dihydroxy-2H-benzo[g]chromene-2-one (114 mg; 0.5 mmole) was mixed with a 40% aqueous solution of glyoxal (288 µL; 2.5 mmole). Acetonitrile (5 mL) was added thereto and the reaction mixture was refluxed for 6 hours. By cooling the solution to room temperature a yellow precipitate was precipitated, which was filtered and washed with acetonitrile. There were obtained 84 mg (68%) of compound 45, which did not need additional purification.

$^1$H-NMR (300 MHz, DMSO-$d_6$) δ/ppm: 4.89 (bs, 1H); 6.34 (bs, 1H); 6.91–8.57 (m, 10H); 9.98 (bs, 2H), 12.19 (bs, 1H); MS m/z: ES$^+$ (water:acetonitrile) [MH]$^+$ 497.2.

Compound 46: 2-Hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one

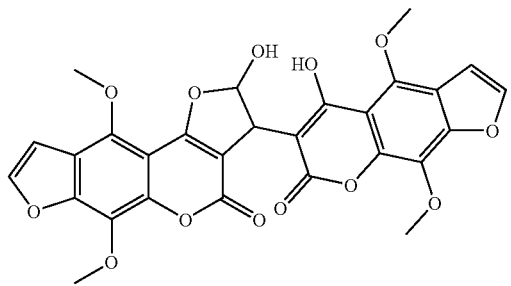

Example 46

5-Hydroxy-4,9-dimethoxy-7-oxo-7H-furo[3,2-g]chromene (131 mg; 0.5 mmole) was mixed with a 40% aqueous solution of glyoxal (230 µL; 2.0 mmole). Acetonitrile (2 mL) was added thereto and the reaction mixture was refluxed for 3 hours. By cooling the solution to room temperature a yellow precipitate was precipitated, which was filtered and washed with acetonitrile. There were obtained 73 mg (52%) of compound 46, which did not need additional purification.

$^1$H-NMR (300 MHz, DMSO-$d_6$) δ/ppm: 4.04 (s, 6H); 4.11 (s, 3H); 4.31 (s, 3H); 4.66 (d, J=3.9 Hz, 1H); 6.24 (bs, 1H); 7.36 (d, J=2.3 Hz, 1H); 7.44 (d, J=2.3 Hz, 1H); 8.12 (d, J=2.3 Hz, 1H); 8.13 (d, J=2.3 Hz, 1H); 8.21 (d, J=6.4 Hz, 1H); 10.67 (bs, 1H); $^{13}$C-NMR (125 MHz, DMSO-$d_6$) δ/ppm: 42.0; 60.1; 60.1; 60.5; 60.6; 97.9; 98.7; 100.7; 100.9; 104.4;

104.7; 107.7; 113.0; 115.2; 126.6; 127.1; 140.7; 143.2; 143.3; 143.3; 145.4; 145.4; 147.8; 147.8; 156.8; 161.7; 164.3; MS m/z: ES+ (water:acetonitrile) [MH]+ 564.8.

Compound 47: 7-Ethyl-3-(7-ethyl-4-hydroxy-2-oxo-2H-chromene-3-yl)-2-hydroxy-2,3-dihydro-4H-furo[3,2-c]chromene-4-one

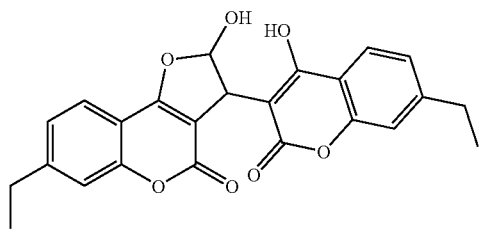

Example 47

7-Ethyl-4-hydroxycoumarin (100 mg; 0.53 mmole) was mixed with a 40% aqueous solution of glyoxal (302 μL; 2.6 mmole). Acetonitrile (5 mL) and the reaction mixture were stirred at room temperature for 9 days. The separated white precipitate was filtered and washed with acetonitrile. There were obtained 24 mg (11%) of compound 47, which did not need additional purification.

$^1$H-NMR (300 MHz, DMSO-d$_6$) δ/ppm: 1.18–1.25 (m, 6H); 2.67–2.77 (m, 4H); 4.77 (d, J=2.9 Hz, 1H); 6.25 (d, J=3.3 Hz, 1H); 7.14–7.31 (m, 4H); 7.67 (d, J=7.8 Hz, 1H); 7.93 (d, J=8.6, 1H); MS m/z: ES+ (acetonitrile:water) [MH]+: 421.0.

Compound 48: 6,8-Dibromo-3-(6,8-dibromo-4-hydroxy-2-oxo-2H-chromene-3-yl)-2-hydroxy-2,3-dihydro-4H-furo[3,2-c]chromene-4-one

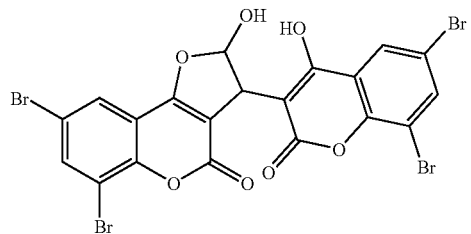

Example 48

6,8-Dibromo-4-hydroxycoumarin (200 mg; 0.62 mmole) was mixed with a 40% aqueous solution of glyoxal (358 μL; 3.12 mmole). Acetonitrile (5 mL) was added thereto and the reaction mixture was refluxed for 24 hours. By cooling the solution to room temperature a white precipitate was precipitated, which was filtered and washed with acetonitrile. There were obtained 10 mg (4.5%) of compound 48, which did not need additional purification.

$^1$H-NMR (300 MHz, DMSO-d$_6$) δ/ppm: 5.69 (s, 1H); 7.67 (s, 1H); 7.67 (d, J=2.3 Hz, 2H); 7.85–7.88 (m, 3H); 8.19 (bs, 1H); 9.26 (bs, 1H); MS m/z: ES− (acetonitrile:water) [M-H]−: 618.8.

Compound 49: 2-Hydroxy-3-(4-hydroxy-6,8-dichloro-2-oxo-2H-chromene-3-yl)-6,8-dichloro-2,3-dihydro-4H-furo[3,2-c]chromene-4-one

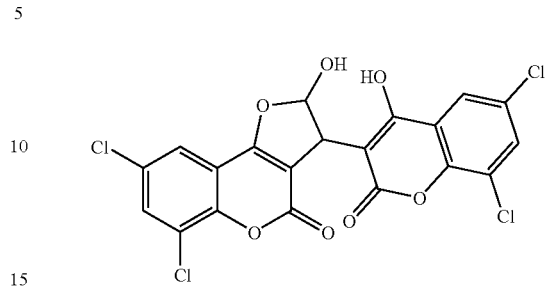

Example 49

4-Hydroxy-6,8-dichlorocoumarin (115.5 mg; 0.5 mmole) was mixed with a 40% aqueous solution of glyoxal (288 μL; 2.5 mmole). Acetonitrile (15 mL) was added thereto and the reaction mixture was refluxed 12 hours. The solvent was evaporated to a minimum volume and then the reaction mixture was diluted with the same volume of water. By cooling overnight at +4° C. a beige precipitate was separated, which was filtered and washed with water. There were obtained 24 mg (19%) of compound 49, which did not need additional purification.

$^1$H-NMR (300 MHz, acetone-d$_6$) δ/ppm: 4.93 (d, J=3.6 Hz, 1H); 6.57 (d, J=3.3 Hz, 1H); 7.70 (d, J=2.3 Hz, 1H); 7.84 (d, J=2.3 Hz, 1H); 7.86 (d, J=2.4 Hz, 1H); 8.01 (d, J=2.3 Hz, 1H); MS m/z: ES− (acetonitrile:water) [M-H]−: 500.9; 502.9; 504.9; 506.4.

Compound 50: 8-Hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one

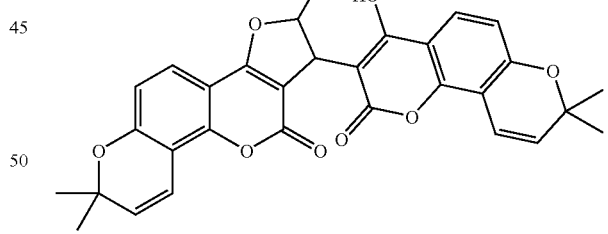

Example 50

4-Hydroxy-8,8-dimethyl-2H,6H-pyrano[2,3-h]chromene-2-one (122 mg; 0.5 mmole) was mixed with a 40% aqueous solution of glyoxal (288 μL; 2.5 mmole). Acetonitrile (3 mL) was added thereto and the reaction mixture was refluxed for 4 hours. The reaction mixture was diluted with water and extracted with ethyl acetate. The organic layers were dried with sodium sulfate and evaporated to dryness. The residue was purified on a silica gel column (10 g) using the eluent chloroform: t-butanol (8:1). There were obtained 96 mg (73%) of compound 50.

¹H-NMR (300 MHz, CDCl₃) δ/ppm: 1.47 (bs, 12H); 5.01 (bs, 1H); 5.71 (d, J=8.9 Hz, 2H); 6.83 (m, 4H); 7.75 (d, J=8.9 Hz, 2H); 9.72 (s, 1H); 11.10 (bs, 2H); MS m/z: ES⁻ (acetonitrile:water) [M-H]⁻: 529.1.

Preparation of the Starting Compounds

Method A

8-Ethyl-4-hydroxycoumarin

A mixture of 2-ethylphenol (Aldrich) (6.1 g; 50 mmole), malonic acid (Aldrich) (5.2 g; 50 mmole), zinc chloride (20.4 g, 150 mmole) and phosphorous oxychloride (Merck) (14 mL; 150 mmole) was heated under stirring for 24 hours at 70–75° C., whereupon the reaction was stopped and a mixture of water and ice was added. The reaction mixture was stirred for further 2 hours at room temperature and then 10% sodium carbonate (150 mL) was added to the filtered brown precipitate while stirring. The insoluble part was filtered and the filtrate was acidified with concentrated hydrochloric acid, whereat a brown precipitate was precipitated, which was then filtered and washed with cold water. By recrystallization from 50% ethanol there were obtained 2.29 g (24%) of brown powdery 8-ethyl-4-hydroxycoumarin.

¹H-NMR (300 MHz, DMSO-d₆) δ/ppm: 1.22 (t, J=7.5 Hz, 3H); 2.78 (q, J=7.5 Hz, 2H); 5.62 (s, 1H); 7.27 (dd, J=7.7 Hz, J=7.7 Hz, 1H); 7.52 (dd, J=7.5 Hz, J=1.6 Hz, 1H); 7.68 (dd, J=7.9 Hz, J=1.6 Hz, 1H); 12.00 (bs, 1H); ¹³C-NMR (75.4 MHz, DMSO-d₆) δ/ppm: 14.0; 22.0; 90.6; 115.5; 120.8; 123.4; 130.9; 132.0; 151.3; 161.7; 165.9.

4-Hydroxy-8-isopropylcoumarin

Starting from 2-isopropylphenol (Aldrich) and by recrystallization of the obtained precipitate from 50% ethanol there were obtained 1.75 g (17.1%) of yellowish powdery 4-hydroxy-8-isopropylcoumarin.

¹H-NMR (300 MHz, DMSO-d₆) δ/ppm: 1.24 (d, J=7.2 Hz, 6H); 3.45 (sept, J=6.9 Hz, 1H); 5.64 (s, 1H); 7.31 (dd, J=7.7 Hz, J=7.7 Hz, 1H); 7.57 (dd, J=7.6 Hz, J=1.6 Hz, 1H); 7.69 (dd, J=7.8 Hz, J=1.6 Hz, 1H); ¹³C-NMR (75.4 MHz, DMSO-d₆) δ/ppm: 22.3; 26.2; 90.6; 115.5; 120.7; 123.5; 129.3; 135.3; 150.7; 161.7; 168.0.

4-Hydroxy-5-isopropyl-8-methylcoumarin

Starting from 5-isopropyl-2-methylphenol (Aldrich) and by trituration of the obtained oil with a mixture of methanol and water there were obtained 853 mg (7.8%) of brown powdery 4-hydroxy-5-isopropyl-8-methylcoumarin.

¹H-NMR (300 MHz, DMSO-d₆) δ/ppm: 1.22 (d, J=6.8 Hz, 6H); 2.31 (s, 3H); 4.26 (sept, J=6.8 Hz, 1H); 5.61 (s, 1H); 7.20 (d, J=7.9 Hz, 1H); 7.43 (d, J=7.9 Hz, 1H); 12.00 (bs, 1H); ¹³C-NMR (75.4 MHz, DMSO-d₆) δ/ppm: 15.1; 24.1; 28.7; 91.5; 112.7; 120.8; 122.9; 132.9; 145.8; 153.0; 161.1; 168.7.

4-Hydroxy-8-chloro-5-methylcoumarin

Starting from 2-chloro-5-methylphenol (Aldrich) and by recrystallization of the obtained precipitate from acetonitrile there were obtained 1.33 g (12.6%) of brown powdery product 4-hydroxy-8-chloro-5-methylcoumarin.

¹H-NMR (300 MHz, DMSO-d₆) δ/ppm: 2.65 (s, 3H); 5.65 (s, 1H); 7.10 (d, J=8.2 Hz, 1H); 7.62 (d, J=8.2 Hz, 1H); 12.60 (bs, 1H); ¹³C-NMR (75.4 MHz, DMSO-d₆) δ/ppm: 22.5; 91.3; 115.8; 117.9; 127.3; 131.5; 136.3; 149.9; 160.3; 168.3.

Method B1

5-Fluoro-4-hydroxycoumarin

A catalytic amount of N-benzyl-benzamide (Aldrich) and dry THF (Aldrich) (20 mL) were put into a three neck flask (inert atmosphere). To the cooled solution (−60° C.), 2.0 M solution of LDA (Aldrich) (10 mmole) in heptane (5 mL) was added. Subsequently, a solution of tert-butyl acetate (Aldrich) (1.3 mL, 10 mmole) dissolved in dry THF (4 mL) was slowly added to the reaction mixture drop by drop and the stirring was continued for 50 minutes at the temperature of −60° C., whereat the colour of solution changed from red-brown to yellow. A solution obtained by dissolving methyl-6-fluorosalicylate (474 mg; 2.4 mmole) in dry THF (10 mL) was added slowly to the carbanion solution and the stirring was continued overnight, whereat the temperature of the reaction mixture reached room temperature. Ethyl acetate (50 mL) and a saturated solution of ammonium chloride (50 mL) were added to the mixture, the layers were separated and then the organic layer was washed with a saturated sodium chloride solution (2×50 mL) and dried with sodium sulfate. The solvent was removed by evaporation under reduced pressure. The remaining brown oily product was mixed with trifluoroacetic acid (3 mL) and the obtained mixture was stirred for 4 hours at room temperature and diluted by a hexane:ether (2:1) solvent mixture (30 mL). A light brown precipitate was precipitated, which by purification on a silica gel column (12 g) using the solvent system chloroform:methanol:acetic acid (60:10:1) yielded 54 mg (12.5%) of light brown amorphous 5-fluoro-4-hydroxycoumarin.

¹H-NMR (300 MHz, DMSO-d₆) δ/ppm: 5.66 (s, 1H); 7.09 (ddd, J=1.0 Hz; J=8.4 Hz, J=11.2 Hz, 1H); 7.17 (m, 1H); 7.64 (dt, J=6.7 Hz, J=8.4 Hz, 1H); 11.00 (bs, 1H); ¹³C-NMR (75.4 MHz, DMSO-d₆) δ/ppm: 93.2; 106.7 (d, J=12.7 Hz); 112.0 (d, J=11.5 Hz); 130.6 (d, J=3.5 Hz); 133.7 (d, J=10.6 Hz); 156.2 (d, J=4.5 Hz); 159.9 (d, J=263.0 Hz); 161.6; 165.7.

Method B2

4-Hydroxy-7-methoxybenzo[g]coumarin

Sodium 3-hydroxy-7-methoxy-2-naphthoate (Fluka) (4.36 g; 20 mmole) was suspended in methanol (50 ml). Concentrated sulfuric acid (3 mL) was added thereto and the reaction mixture was kept heating under reflux for 5 hours and then it was cooled to room temperature. Ethyl acetate (100 mL) and a saturated sodium bicarbonate solution (100 mL) were added to the mixture. After stirring the layers were separated and the organic layer was washed once again with a saturated sodium bicarbonate solution (100 mL). After drying with sodium sulfate the solvent was evaporated under reduced pressure. In the flask a crystalline product (3.1 g, 67%) remained, which, in accordance with the process described under method B1 and by recrystallization from methanol, yielded 1.4 g (58%) of light brown crystalline 4-hydroxy-7-methoxybenzo[g]coumarin.

¹H-NMR (300 MHz, DMSO-d₆) δ/ppm: 3.89 (s, 3H); 5.65 (s, 1H); 7.30 (dd, J=2.5 Hz; J=9.0 Hz, 1H); 7.54 (d, J=2.4 Hz, 1H); 7.81 (s, 1H); 7.91 (d, J=9.0 Hz, 1H); 8.35 (s, 1H); 12.59 (bs, 1H);

MS m/z: ES⁻ (acetonitrile:water); [M-H]⁻ 241.1.

Method B3

4-Hydroxy-9-methoxybenzo[g]coumarin

Methyl 3,5-dihydroxy-2-naphthoate (3.27 g; 15 mmole) was mixed with potassium carbonate (3 g; 22 mmole), acetone (50 µL) was added and then dimethylsulfate (Merck) (1.56 mL; 16.5 mmole) was slowly added drop by drop. The reaction mixture was refluxed for 2 hours, cooled to room temperature and water (100 mL) was added thereto, whereat all potassium carbonate was dissolved. Dichloromethane (100 mL) was added to the solution and the layers were separated. The organic layer was dried over anhydrous sodium sulfate and the solvent was evaporated to dryness. The solid residue was recrystallized from methanol and 2.4 g (70%) of methyl 3-hydroxy-5-methoxy-2-naphthoate were obtained.

$^1$H-NMR (300 MHz, DMSO-d$_6$) δ/ppm: 3.93 (s, 3H); 3.95 (s, 3H); 7.00 (d, J=7.5 Hz, 1H); 7.28 (t, J=8.0 Hz, 1H); 7.51 (s, 1H); 7.53 (d, J=9.0 Hz, 1H); 8.41 (s, 1H).

The treatment of methyl 3-hydroxy-5-methoxy-2-naphthoate according to the process described under Method B2 yielded 1.0 g (84%) of 4-hydroxy-9-methoxy-benzo[g]coumarin.

$^1$H-NMR (300 MHz, DMSO-d$_6$) δ/ppm: 3.99 (s, 3H); 5.66 (s, 1H); 7.06 (d, J=7.6 Hz, 1H); 7.44 (t, J=7.9 Hz, 1H); 7.67 (d, =8.3 Hz, 1H); 7.87 (s, 1H); 8.41 (s, 1H); 12.67 (bs, 1H); MS m/z: ES$^-$ (acetonitrile:water); [M-H]$^-$ 241.1.

Method B4

4,7-Dihydroxy-benzo[g]coumarin

A suspension of methyl 3,7-dihydroxy-2-naphthoate (2.2 g; 10 mmole), benzylchloride (Merck) (1.26 mL; 11.0 mmole), potassium iodide (1.8 g; 11.0 mmole) and potassium carbonate (2.0 g; 15 mmole) in acetone (30 mL) was refluxed for 7 hours and then cooled to room temperature. The inorganic precipitate was filtered off and washed with acetone, whereas the filtrate was evaporated to dryness The solid residue was dissolved in ethyl acetate and the resulting solution was washed with 1M hydrochloric acid. After drying with sodium sulfate the organic layer was evaporated and the dry residue was recrystallized from methanol, whereat 1.2 g (39%) of methyl-7-benzyloxy-3-hydroxy-2-naphthoate were obtained.

$^1$H-NMR (300 MHz, DMSO-d$_6$) δ/ppm: 3.95 (s, 3H); 5.20 (s, 2H); 7.29–7.45 (m, 5H); 7.51–7.56 (m, 3H); 7.73 (d, J=9.3 Hz, 1H); 8.37 (s, 1H); 10.08 (bs, 1H); MS m/z: ES$^+$ (acetonitrile:water); [MH]$^+$ 309.2.

The obtained methyl-7-benzyloxy-3-hydroxy-2-naphthoate was treated according to the process described under Method B1 and there were obtained 1.1 g (91%) of 7-benzyloxy-4-hydroxybenzo[g]coumarin.

$^1$H-NMR (300 MHz, DMSO-d$_6$) δ/ppm: 5.23 (s, 2H); 5.65 (s, 1H); 7.36–7.45 (m, 6H); 7.53 (d, J=6.8 Hz, 3H); 7.81 (s, 1H); 7.93 (d, J=6.7 Hz, 1H); 8.33 (s, 1H); 12.61 (bs, 1H).

7-Benzyloxy-4-hydroxybenzo[g]coumarin (1 g; 3.14 mmole) was dissolved in ethanol (100 mL) and cyclohexene (Merck) (1.54 mL) and 10% palladium on active charcoal (150 mg) were added thereto. The reaction mixture was refluxed for 5 hours. The catalyst was filtered off and washed with ethanol, whereas the filtrate was evaporated to a dry residue. The solid residue was recrystallized from ethyl acetate, whereat 263 mg (33%) of 4,7-dihydroxy-benzo[g]coumarin were obtained.

$^1$H-NMR (300 MHz, DMSO-d$_6$) δ/ppm: 5.63 (s, 1H); 7.22 (dd, J=2.4 Hz, J=8.9 Hz, 1H); 7.30 (d, J=2.1 Hz, 1H); 7.74 (s, 1H); 7.85 (d, J=9.0 Hz, 1H); 8.21 (s, 1H); 9.88 (bs, 1H); 12.53 (bs, 1H); MS m/z: ES$^+$ (acetonitrile:water); [MH]$^+$ 229.2.

4,9-Dihydroxy-benzo[g]coumarin

Starting from methyl 3,5-dihydroxy-2-naphthoate according to the process described under Method B4 there were obtained 267 mg (8%) of methyl 5-benzoxy-3-hydroxy-2-naphthoate, $^1$H-NMR (300 MHz, DMSO-d$_6$) δ/ppm: 3.87 (s, 3H); 5.31 (s, 2H); 7.12 (d, J=7.2 Hz, 1H); 7.27–7.56 (m, 8H); 7.74 (s, 1H); 10.25 (bs, 1H), which by cyclization yielded 1.28 g (82%) of 9-benzyloxy-4-hydroxybenzo[g]coumarin, MS m/z: ES$^-$ (acetonitrile:water); [M-H]$^-$ 317.2.

By debenzylation of 9-benzyloxy-4-hydroxybenzo[g]coumarin there were obtained 275 mg (74%) of 4,9-dihydroxybenzo[g]coumarin.

$^1$H-NMR (300 MHz, DMSO-d$_6$) δ/ppm: 5.66 (s, 1H); 6.96 (dd, J=2.4 Hz, J=9.0 Hz, 1H); 7.33 (t, J=7.6 Hz, 1H); 7.56 (d, J=8.5 Hz, 1H); 7.88 (s, 1H); 8.38 (s, 1H); 10.37 (bs, 1H); 12.62 (bs, 1H).

Method C

4-Hydroxy-6,8-diisopropylcoumarin

To a solution of 3,5-diisopropylsalicylic acid (Aldrich) (10 mmole, 2.2 g) and dichloromethane (20 mL), oxalylchloride (Merck) (11.0 mmole, 1.03 mL) and DMF (Aldrich) (80 µL) were added. The reaction mixture was refluxed for 1 hour, whereupon the solvent and the excess of oxalylchloride were removed under reduced pressure. The obtained oily product was dissolved in dichloromethane (50 mL) and ammonia gas was introduced into reaction mixture under cooling. The solution was diluted with water and, after drying with sodium sulfate, the organic layer was evaporated under reduced pressure. A yellow residue was recrysatallized from n-hexane, whereat there were obtained 876 mg (40%) of 3,5-diisopropyl salicylamide in the form of a white crystalline product:

$^1$H-NMR (300 MHz, CDCl$_3$) δ/ppm: 1.22 (d, J=6.9 Hz, 6H); 1.23 (d, J=6.9 Hz, 6H); 2.83 (sept, J=6.9 Hz, 1H); 3.38 (sept, J=6.9 Hz, 1H); 5.80 (bs, 2H); 7.00 (d, J=2.1 Hz, 1H); 7.22 (d, J=2.1 Hz, 1H); 12.00 (bs, 1H).

To a solution of phosphorous oxychloride (1.35 g, 8.8 mmole) and dry pyridine (12 mL) cooled to 0° C., a solution of 3,5-diisopropyl salicylamide (1.10 g, 5 mmole) and dry pyridine (5 mL) was slowly added drop by drop. The reaction mixture was stirred at room temperature, whereat the colour changed from colourless over violet to red. After extraction with ethyl acetate and washing with a saturated sodium chloride solution and 2N hydrochloric acid, the organic layer was dried and evaporated under reduced pressure. The obtained solid residue was recrystallized from acetonitrile, whereat there were obtained 610 mg (60%) of 2-hydroxy-3,5-diisopropyl benzonitrile.

$^1$H-NMR (300 MHz, DMSO-d$_6$) δ/ppm: 1.15 (d, J=6.9 Hz, 6H); 1.19 (d, J=6.9 Hz, 6H); 2.90 (sept, J=6.9 Hz, 1H); 3.52 (sept, J=6.9 Hz, 1H); 7.48 (d, J=2.2 Hz, 1H); 7.50 (d, J=2.2 Hz, 1H); IR (KBr): 2234 cm$^{-1}$.

To dry THF (10 mL) there was added 3.0 M solution of methylmagnesium bromide in diethylether (Aldrich) (10.9 mL; 32.8 mmole) and then a previously prepared solution of 2-hydroxy-3,5-diisopropyl benzonitrile (2.78 g, 13.7 mmole) and dry THF (70 mL) was added. After 7 hours under the reflux the reaction mixture was mixed with water (100 mL), acidified with concentrated hydrochloric acid (50 mL) and refluxed for one more hour. After cooling and extraction with ethyl acetate an oily product was obtained, which was purified on a silica gel column, whereat there were obtained 380 mg (12.5%) of 2'-hydroxy-3'5'-diisopropylacetophenone:

$^1$H-NMR (300 MHz, CDCl$_3$) δ/ppm: 1.23 (d, J=6.9 Hz, 6H); 1.25 (d, J=6.9 Hz, 6H); 2.64 (s, 3H); 2.87 (sept, J=6.9 Hz, 1H); 3.36 (sept, J=6.9 Hz, 1H); 7.29 (d, J=2.2 Hz, 1H); 7.40 (d, J=2.2 Hz, 1H), 12.55 (s, 1H).

2'-Hydroxy-3'5'-diisopropylacetophenone (380 mg, 1.7 mmole) was dissolved in diethylcarbonate (Aldrich) (5 mL) and the reaction mixture was cooled to 0° C. Subsequently, a 60% suspension of sodium hydride in mineral oil (Aldrich) (165 mg, 4.1 mmole) was added in small portions After 1 hour of reflux the reaction mixture was cooled, mixed with water (40 mL) and extracted with diethylether (2×20 mL). The aqueous extract was acidified and extracted with ethyl acetate. The organic extract was dried with sodium sulfate and the solvent was evaporated under reduced pressure, whereat there were obtained 305 mg of a yellow powder, which was purified on a silica gel column, whereat there were obtained 240 mg (57%) of white crystalline 4-hydroxy-6,8-diisopropylcoumarin.

$^1$H-NMR (300 MHz, DMSO-d$_6$) δ/ppm: 1.23 (d, J=6.9 Hz, 6H); 1.26 (d, J=6.9 Hz, 6H); 2.98 (sept, J=6.9 Hz, 1H); 3.41 (sept, J=6.9 Hz, 1H); 5.59 (s, 1H); 7.44 (d, J=2.2 Hz, 1H); 7.51 (d, J=2.2 Hz, 1H), 12.3 (bs, 1H).

The invention claimed is:

1. A compound of the formula (I)

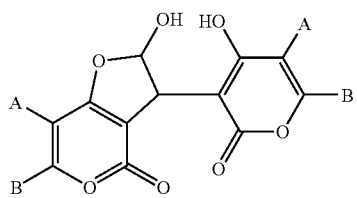

(I)

wherein

A and B taken together with the carbon atoms to which they are attached, each independently represent an aromatic moiety or a heteroaromatic moiety, wherein the compound of the formula (I) is selected from the group consisting of:

2-hydroxy-3-(4-hydroxy-5-methyl-2-oxo-2H-chromene-3-yl)-9-methyl-2,3-dihydro-4H-furo[3,2-c]chromene-4-one;

2-hydroxy-3-(4-hydroxy-6-methyl-2-oxo-2H-chromene-3-yl)-8-methyl-2,3-dihydro-4H-furo[3,2-c]chromene-4-one;

2-hydroxy-3-(4-hydroxy-7-methyl-2-oxo-2H-chromene-3-yl)-7-methyl-2,3-dihydro-4H-furo[3,2-c]chromene-4-one;

2-hydroxy-3-(4-hydroxy-8-methyl-2-oxo-2H-chromene-3-yl)-6-methyl-2,3-dihydro-4H-furo[3,2-c]chromene-4-one;

2-hydroxy-3-(4-hydroxy-5,7-dimethyl-2-oxo-2H-chromene-3-yl)-7,9-dimethyl-2,3-dihydro-4H-furo[3,2-c]chromene-4-one;

2-hydroxy-3-(4-hydroxy-5,8-dimethyl-2-oxo-2H-chromene-3-yl)-6,9-dimethyl-2,3-dihydro-4H-furo[3,2-c]chromene-4-one;

2-hydroxy-3-(4-hydroxy-6,7-dimethyl-2-oxo-2H-chromene-3-yl)-7,8-dimethyl-2,3-dihydro-4H-furo[3,2-c]chromene-4-one;

2-hydroxy-3-(4-hydroxy-7,8-dimethyl-2-oxo-2H-chromene-3-yl)-6,7-dimethyl-2,3-dihydro-4H-furo[3,2-c]chromene-4-one;

2-hydroxy-3-(4-hydroxy-6,8-dimethyl-2-oxo-2H-chromene-3-yl)-6,8-dimethyl-2,3-dihydro-4H-furo[3,2-c]chromene-4-one;

8-ethyl-3-(6-ethyl-4-hydroxy-2-oxo-2H-chromene-3-yl)-2-hydroxy-2,3-dihydro-4H-furo[3,2-c]chromene-4-one;

6-ethyl-3-(8-ethyl-4-hydroxy-2-oxo-2H-chromene-3-yl)-2-hydroxy-2,3-dihydro-4H-furo[3,2-c]chromene-4-one;

2-hydroxy-3-(4-hydroxy-6-isopropyl-2-oxo-2H-chromene-3-yl)-8-isopropyl-2,3-dihydro-4H-furo[3,2-c]chromene-4-one;

2-hydroxy-3-(4-hydroxy-8-isopropyl-2-oxo-2H-chromene-3-yl)-6-isopropyl-2,3-dihydro-4H-furo[3,2-c]chromene-4-one;

2-hydroxy-3-(4-hydroxy-6,8-diisopropyl-2-oxo-2H-chromene-3-yl)-6,8-diisopropyl-2,3-dihydro-4H-furo[3,2-c]chromene-4-one;

2-hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one;

2-hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one;

2-hydroxy-3-(4-hydroxy-5-methoxy-2-oxo-2H-chromene-3-yl)-9-methoxy-2,3-dihydro-4H-furo[3,2-c]chromene-4-one;

2-hydroxy-3-(4-hydroxy-6-methoxy-2-oxo-2H-chromene-3-yl)-8-methoxy-2,3-dihydro-4H-furo[3,2-c]chromene-4-one;

2-hydroxy-3-(4-hydroxy-7-methoxy-2-oxo-2H-chromene-3-yl)-7-methoxy-2,3-dihydro-4H-furo[3,2-c]chromene-4-one;

2-hydroxy-3-(4-hydroxy-8-methoxy-2-oxo-2H-chromene-3-yl)-6-methoxy-2,3-dihydro-4H-furo[3,2-c]chromene-4-one;

2-hydroxy-3-(4-hydroxy-5,7-dimethoxy-2-oxo-2H-chromene-3-yl)-7,9-dimethoxy-2,3-dihydro-4H-furo[3,2-c]chromene-4-one;

2-hydroxy-3-(4-hydroxy-6,7-dimethoxy-2-oxo-2H-chromene-3-yl)-7,8-dimethoxy-2,3-dihydro-4H-furo[3,2-c]chromene-4-one;

3-(4,5-dihydroxy-2-oxo-2H-chromene-3-yl)-2,9-dihydroxy-2,3-dihydro-4H-furo[3,2-c]chromene-4-one;

3-(4,6-dihydroxy-2-oxo-2H-chromene-3-yl)-2,8-dihydroxy-2,3-dihydro-4H-furo[3,2-c]chromene-4-one;

3-(4,7-dihydroxy-8-methyl-2-oxo-2H-chromene-3-yl)-2,7-dihydroxy-6-methyl-2,3-dihydro-4H-furo[3,2-c]chromene-4-one;

3-(4,7-dihydroxy-5-methyl-2-oxo-2H-chromene-3-yl)-2,7-dihydroxy-9-methyl-2,3-dihydro-4H-furo[3,2-c]chromene-4-one;

9-fluoro-3-(5-fluoro-4-hydroxy-2-oxo-2H-chromene-3-yl)-2-hydroxy-2,3-dihydro-4H-furo[3,2-c]chromene-4-one;

8-fluoro-3-(6-fluoro-4-hydroxy-2-oxo-2H-chromene-3-yl)-2-hydroxy-2,3-dihydro-4H-furo[3,2-c]chromene-4-one;

2-hydroxy-3-(4-hydroxy-6-chloro-2-oxo-2H-chromene-
3-yl)-8-chloro-2,3-dihydro-4H-furo[3,2-c]chromene-
4-one;
8-bromo-3-(6-bromo-4-hydroxy-2-oxo-2H-chromene-3-
yl)-2-hydroxy-2,3-dihydro-4H-furo[3,2-c]chromene-4-
one;
2-hydroxy-3-(4-hydroxy-6-iodo-2-oxo-2H-chromene-3-
yl)-8-iodo-2,3-dihydro-4H-furo[3,2-c]chromene-4-
one;
7-fluoro-3-(7-fluoro-4-hydroxy-2-oxo-2H-chromene-3-
yl)-2-hydroxy-2,3-dihydro-4H-furo[3,2-c]chromene-4-
one;
2-hydroxy-3-(4-hydroxy-7-chloro-2-oxo-2H-chromene-
3-yl)-7-chloro-2,3-dihydro-4H-furo[3,2-c]chromene-
4-one;
2-hydroxy-3-(4-hydroxy-8-chloro-2-oxo-2H-chromene-
3-yl)-6-chloro-2,3-dihydro-4H-furo[3,2-c]chromene-
4-one;
2-hydroxy-3-(4-hydroxy-6-chloro-7-methyl-2-oxo-2H-
chromene-3-yl)-8-chloro-7-methyl-2,3-dihydro-4H-
furo[3,2-c]chromene-4-one;
2-hydroxy-3-(1-hydroxy-3-oxo-3H-benzo[f]chromene-2-
yl)-2,3-dihydro-4H-benzo[f]furo[3,2-c]chromene-4-
one;
2-hydroxy-3-(4-hydroxy-2-oxo-2H-benzo[g]chromene-
3-yl)-2,3-dihydro-4H-benzo[g]furo[3,2-c]chromene-4-
one;
2-hydroxy-1-(4-hydroxy-2-oxo-2H-benzo[h]chromene-
3-yl)-1,2-dihydro-11H-benzo[h]furo[3,2-c]chromene-
11-one;
2-hydroxy-3-(4-hydroxy-7-methoxy-2-oxo-2H-benzo[g]
chromene-2-yl)-9-methoxy-2,3-dihydro-4H-benzo[g]
furo[3,2-c]chromene-4-one;
2-hydroxy-3-(4-hydroxy-9-methoxy-2-oxo-2H-benzo[g]
chromene-2-yl)-7-methoxy-2,3-dihydro-4H-benzo[g]
furo[3,2-c]chromene-4-one;
3-(4,9-dihydroxy-2-oxo-2H-benzo[g]chromene-2-yl)-2,
7-dihydroxy-2,3-dihydro-4H-benzo[g]furo[3,2-c]
chromene-4-one;
3-(4,7-dihydroxy-2-oxo-2H-benzo[g]chromene-2-yl)-2,
9-dihydroxy-2,3-dihydro-4H-benzo[g]furo[3,2-c]
chromene-4-one;
2-hydroxy-3-(5-hydroxy-4,9-dimethoxy-7-oxo-7H-furo
[3,2-g]chromene-6-yl)-6,10-dimethoxy-2,3-dihydro-
4H-bisfuro[3,2-c;3,2-g]chromene-4-one;
7-ethyl-3-(7-ethyl-4-hydroxy-2-oxo-2H-chromene-3-
yl)-2-hydroxy-2,3-dihydro-4H-furo[3,2-c]
chromene-4-one;
6,8-dibromo-3-(6,8-dibromo-4-hydroxy-2-oxo-2H-
chromene-3-yl)-2-hydroxy-2,3-dihydro-4H-furo[3,
2-c]chromene-4-one;
2-hydroxy-3-(4-hydroxy-6,8-dichloro-2-oxo-2H-
chromene-3-yl)-6,8-dichloro-2,3-dihydro-4H-furo
[3,2-c]chromene-4-one;
8-hydroxy-7-(4-hydroxy-8,8-dimethyl-2-oxo-2H,7H-
pyrano[2,3-h]chromene-3-yl)-2,2-dimethyl-7,8-di-
hydro-2H,6H-pyrano[2,3-h]furo[3,2-c]chromene-6-
one, and
stereoisomers, tautomers, pharmaceutically acceptable salts
and solvates thereof.

2. A process for the preparing a compound of formula (I)

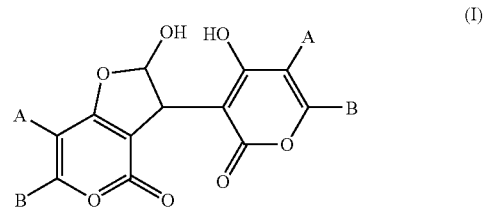

wherein
A and B taken together with the carbon atoms to which
they are attached, each independently represent an
aromatic moiety or a heteroaromatic moiety,
wherein the compound of formula (I) is selected from the
group consisting of:
2-hydroxy-3-(4-hydroxy-5-methyl-2-oxo-2H-chromene-
3-yl)-9-methyl-2,3-dihydro-4H-furo[3,2-c]chromene-
4-one;
2-hydroxy-3-(4-hydroxy-6-methyl-2-oxo-2H-chromene-
3-yl)-8-methyl-2,3-dihydro-4H-furo[3,2-c]chromene-
4-one;
2-hydroxy-3-(4-hydroxy-7-methyl-2-oxo-2H-chromene-
3-yl)-7-methyl-2,3-dihydro-4H-furo[3,2-c]chromene-
4-one;
2-hydroxy-3-(4-hydroxy-8-methyl-2-oxo-2H-chromene-
3-yl)-6-methyl-2,3-dihydro-4H-furo[3,2-c]chromene-
4-one;
2-hydroxy-3-(4-hydroxy-5,7-dimethyl-2-oxo-2H-
chromene-3-yl)-7,9-dimethyl-2,3-dihydro-4H-furo[3,
2-c]chromene-4-one;
2-hydroxy-3-(4-hydroxy-5,8-dimethyl-2-oxo-2H-
chromene-3-yl)-6,9-dimethyl-2,3-dihydro-4H-furo[3,
2-c]chromene-4-one;
2-hydroxy-3-(4-hydroxy-6,7-dimethyl-2-oxo-2H-
chromene-3-yl)-7,8-dimethyl-2,3-dihydro-4H-furo[3,
2-c]chromene-4-one;
2-hydroxy-3-(4-hydroxy-7,8-dimethyl-2-oxo-2H-
chromene-3-yl)-6,7-dimethyl-2,3-dihydro-4H-furo[3,
2-c]chromene-4-one;
2-hydroxy-3-(4-hydroxy-6,8-dimethyl-2-oxo-2H-
chromene-3-yl)-6,8-dimethyl-2,3-dihydro-4H-furo[3,
2-c]chromene-4-one;
8-ethyl-3-(6-ethyl-4-hydroxy-2-oxo-2H-chromene-3-yl)-
2-hydroxy-2,3-dihydro-4H-furo[3,2-c]chromene-4-
one;
6-ethyl-3-(8-ethyl-4-hydroxy-2-oxo-2H-chromene-3-yl)-
2-hydroxy-2,3-dihydro-4H-furo[3,2-c]chromene-4-
one;
2-hydroxy-3-(4-hydroxy-6-isopropyl-2-oxo-2H-
chromene-3-yl)-8-isopropyl-2,3-dihydro-4H-furo[3,2-
c]chromene-4-one;
2-hydroxy-3-(4-hydroxy-8-isopropyl-2-oxo-2H-
chromene-3-yl)-6-isopropyl-2,3-dihydro-4H-furo[3,2-
c]chromene-4-one;
2-hydroxy-3-(4-hydroxy-6,8-diisopropyl-2-oxo-2H-
chromene-3-yl)-6,8-diisopropyl-2,3-dihydro-4H-furo
[3,2-c]chromene-4-one;
2-hydroxy-3-(4-hydroxy-5-isopropyl-8-methyl-2-oxo-
2H-chromene-3-yl)-9-isopropyl-6-methyl-2,3-dihy-
dro-4H-furo[3,2-c]chromene-4-one;
2-hydroxy-3-(4-hydroxy-8-isopropyl-5-methyl-2-oxo-
2H-chromene-3-yl)-6-isopropyl-9-methyl-2,3-dihy-
dro-4H-furo[3,2-c]chromene-4-one;

2-hydroxy-3-(4-hydroxy-5-methoxy-2-oxo-2H-chromene-3-yl)-9-methoxy-2,3-dihydro-4H-furo[3,2-c]chromene-4-one;
2-hydroxy-3-(4-hydroxy-6-methoxy-2-oxo-2H-chromene-3-yl)-8-methoxy-2,3-dihydro-4H-furo[3,2-c]chromene-4-one;
2-hydroxy-3-(4-hydroxy-7-methoxy-2-oxo-2H-chromene-3-yl)-7-methoxy-2,3-dihydro-4H-furo[3,2-c]chromene-4-one;
2-hydroxy-3-(4-hydroxy-8-methoxy-2-oxo-2H-chromene-3-yl)-6-methoxy-2,3-dihydro-4H-furo[3,2-c]chromene-4-one;
2-hydroxy-3-(4-hydroxy-5,7-dimethoxy-2-oxo-2H-chromene-3-yl)-7,9-dimethoxy-2,3-dihydro-4H-furo[3,2-c]chromene-4-one;
2-hydroxy-3-(4-hydroxy-6,7-dimethoxy-2-oxo-2H-chromene-3-yl)-7,8-dimethoxy-2,3-dihydro-4H-furo[3,2-c]chromene-4-one;
3-(4,5-dihydroxy-2-oxo-2H-chromene-3-yl)-2,9-dihydroxy-2,3-dihydro-4H-furo[3,2-c]chromene-4-one;
3-(4,6-dihydroxy-2-oxo-2H-chromene-3-yl)-2,8-dihydroxy-2,3-dihydro-4H-furo[3,2-c]chromene-4-one;
3-(4,7-dihydroxy-8-methyl-2-oxo-2H-chromene-3-yl)-2,7-dihydroxy-6-methyl-2,3-dihydro-4H-furo[3,2-c]chromene-4-one;
3-(4,7-dihydroxy-5-methyl-2-oxo-2H-chromene-3-yl)-2,7-dihydroxy-9-methyl-2,3-dihydro-4H-furo[3,2-c]chromene-4-one;
9-fluoro-3-(5-fluoro-4-hydroxy-2-oxo-2H-chromene-3-yl)-2-hydroxy-2,3-dihydro-4H-furo[3,2-c]chromene-4-one;
8-fluoro-3-(6-fluoro-4-hydroxy-2-oxo-2H-chromene-3-yl)-2-hydroxy-2,3-dihydro-4H-furo[3,2-c]chromene-4-one;
2-hydroxy-3-(4-hydroxy-6-chloro-2-oxo-2H-chromene-3-yl)-8-chloro-2,3-dihydro-4H-furo[3,2-c]chromene-4-one;
8-bromo-3-(6-bromo-4-hydroxy-2-oxo-2H-chromene-3-yl)-2-hydroxy-2,3-dihydro-4H-furo[3,2-c]chromene-4-one;
2-hydroxy-3-(4-hydroxy-6-iodo-2-oxo-2H-chromene-3-yl)-8-iodo-2,3-dihydro-4H-furo[3,2-c]chromene-4-one;
7-fluoro-3-(7-fluoro-4-hydroxy-2-oxo-2H-chromene-3-yl)-2-hydroxy-2,3-dihydro-4H-furo[3,2-c]chromene-4-one;
2-hydroxy-3-(4-hydroxy-7-chloro-2-oxo-2H-chromene-3-yl)-7-chloro-2,3-dihydro-4H-furo[3,2-c]chromene-4-one;
2-hydroxy-3-(4-hydroxy-8-chloro-2-oxo-2H-chromene-3-yl)-6-chloro-2,3-dihydro-4H-furo[3,2-c]chromene-4-one;
2-hydroxy-3-(4-hydroxy-6-chloro-7-methyl-2-oxo-2H-chromene-3-yl)-8-chloro-7-methyl-2,3-dihydro-4H-furo[3,2-c]chromene-4-one;
2-hydroxy-3-(1-hydroxy-3-oxo-3H-benzo[f]chromene-2-yl)-2,3-dihydro-4H-benzo[f]furo[3,2-c]chromene-4-one;
2-hydroxy-3-(4-hydroxy-2-oxo-2H-benzo[g]chromene-3-yl)-2,3-dihydro-4H-benzo[g]furo[3,2-c]chromene-4-one;
2-hydroxy-1-(4-hydroxy-2-oxo-2H-benzo[h]chromene-3-yl)-1,2-dihydro-11H-benzo[h]furo[3,2-c]chromene-11-one;
2-hydroxy-3-(4-hydroxy-7-methoxy-2-oxo-2H-benzo[g]chromene-2-yl)-9-methoxy-2,3-dihydro-4H-benzo[g]furo[3,2-c]chromene-4-one;
2-hydroxy-3-(4-hydroxy-9-methoxy-2-oxo-2H-benzo[g]chromene-2-yl)-7-methoxy-2,3-dihydro-4H-benzo[g]furo[3,2-c]chromene-4-one;
3-(4,9-dihydroxy-2-oxo-2H-benzo[g]chromene-2-yl)-2,7-dihydroxy-2,3-dihydro-4H-benzo[g]furo[3,2-c]chromene-4-one;
3-(4,7-dihydroxy-2-oxo-2H-benzo[g]chromene-2-yl)-2,9-dihydroxy-2,3-dihydro-4H-benzo[g]furo[3,2-c]chromene-4-one;
2-hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one;
7-ethyl-3-(7-ethyl-4-hydroxy-2-oxo-2H-chromene-3-yl)-2-hydroxy-2,3-dihydro-4H-furo[3,2-c]chromene-4-one;
6,8-dibromo-3-(6,8-dibromo-4-hydroxy-2-oxo-2H-chromene-3-yl)-2-hydroxy-2,3-dihydro-4H-furo[3,2-c]chromene-4-one;
2-hydroxy-3-(4-hydroxy-6,8-dichloro-2-oxo-2H-chromene-3-yl)-6,8-dichloro-2,3-dihydro-4H-furo[3,2-c]chromene-4-one;
8-hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one, and stereoisomers, tautomers, pharmaceutically acceptable salts and solvates thereof, comprising reacting a compound of the formula (II) or a salt thereof

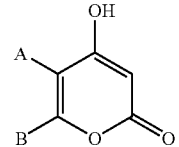
(II)

with glyoxal of the formula (III)

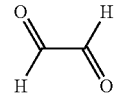
(III)

in an aqueous-organic medium at a reaction temperature of from about room temperature to about 90° C.

3. The process according to claim 2, wherein the aqueous-organic medium comprises acetonitrde.

4. The process according to claim 3, wherein the reaction temperature is the boiling temperature of acetonitrile.

5. A pharmaceutical composition comprising a compound selected from the group consisting of:
2-hydroxy-3-(4-hydroxy-5-methyl-2-oxo-2H-chromene-3-yl)-9-methyl-2,3-dihydro-4H-furo[3,2-c]chromene-4-one;
2-hydroxy-3-(4-hydroxy-6-methyl-2-oxo-2H-chromene-3-yl)-8-methyl-2,3-dihydro-4H-furo[3,2-c]chromene-4-one;
2-hydroxy-3-(4-hydroxy-7-methyl-2-oxo-2H-chromene-3-yl)-7-methyl-2,3-dihydro-4H-furo[3,2-c]chromene-4-one;
2-hydroxy-3-(4-hydroxy-8-methyl-2-oxo-2H-chromene-3-yl)-6-methyl-2,3-dihydro-4H-furo[3,2-c]chromene-4-one;

2-hydroxy-3-(4-hydroxy-5,7-dimethyl-2-oxo-2H-chromene-3-yl)-7,9-dimethyl-2,3-dihydro-4H-furo[3,2-c]chromene-4-one;
2-hydroxy-3-(4-hydroxy-5,8-dimethyl-2-oxo-2H-chromene-3-yl)-6,9-dimethyl-2,3-dihydro-4H-furo[3,2-c]chromene-4-one;
2-hydroxy-3-(4-hydroxy-6,7-dimethyl-2-oxo-2H-chromene-3-yl)-7,8-dimethyl-2,3-dihydro-4H-furo[3,2-c]chromene-4-one;
2-hydroxy-3-(4-hydroxy-7,8-dimethyl-2-oxo-2H-chromene-3-yl)-6,7-dimethyl-2,3-dihydro-4H-furo[3,2-c]chromene-4-one;
2-hydroxy-3-(4-hydroxy-6,8-dimethyl-2-oxo-2H-chromene-3-yl)-6,8-dimethyl-2,3-dihydro-4H-furo[3,2-c]chromene-4-one;
8-ethyl-3-(6-ethyl-4-hydroxy-2-oxo-2H-chromene-3-yl)-2-hydroxy-2,3-dihydro-4H-furo[3,2-c]chromene-4-one;
6-ethyl-3-(8-ethyl-4-hydroxy-2-oxo-2H-chromene-3-yl)-2-hydroxy-2,3-dihydro-4H-furo[3,2-c]chromene-4-one;
2-hydroxy-3-(4-hydroxy-6-isopropyl-2-oxo-2H-chromene-3-yl)-8-isopropyl-2,3-dihydro-4H-furo[3,2-c]chromene-4-one;
2-hydroxy-3-(4-hydroxy-8-isopropyl-2-oxo-2H-chromene-3-yl)-6-isopropyl-2,3-dihydro-4H-furo[3,2-c]chromene-4-one;
2-hydroxy-3-(4-hydroxy-6,8-diisopropyl-2-oxo-2H-chromene-3-yl)-6,8-diisopropyl-2,3-dihydro-4H-furo[3,2-c]chromene-4-one;
2-hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one;
2-hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one;
2-hydroxy-3-(4-hydroxy-5-methoxy-2-oxo-2H-chromene-3-yl)-9-methoxy-2,3-dihydro-4H-furo[3,2-c]chromene-4-one;
2-hydroxy-3-(4-hydroxy-6-methoxy-2-oxo-2H-chromene-3-yl)-8-methoxy-2,3-dihydro-4H-furo[3,2-c]chromene-4-one;
2-hydroxy-3-(4-hydroxy-7-methoxy-2-oxo-2H-chromene-3-yl)-7-methoxy-2,3-dihydro-4H-furo[3,2-c]chromene-4-one;
2-hydroxy-3-(4-hydroxy-8-methoxy-2-oxo-2H-chromene-3-yl)-6-methoxy-2,3-dihydro-4H-furo[3,2-c]chromene-4-one;
2-hydroxy-3-(4-hydroxy-5,7-dimethoxy-2-oxo-2H-chromene-3-yl)-7,9-dimethoxy-2,3-dihydro-4H-furo[3,2-c]chromene-4-one;
2-hydroxy-3-(4-hydroxy-6,7-dimethoxy-2-oxo-2H-chromene-3-yl)-7,8-dimethoxy-2,3-dihydro-4H-furo[3,2-c]chromene-4-one;
3-(4,5-dihydroxy-2-oxo-2H-chromene-3-yl)-2,9-dihydroxy-2,3-dihydro-4H-furo[3,2-c]chromene-4-one;
3-(4,6-dihydroxy-2-oxo-2H-chromene-3-yl)-2,8-dihydroxy-2,3-dihydro-4H-furo[3,2-c]chromene-4-one;
3-(4,7-dihydroxy-8-methyl-2-oxo-2H-chromene-3-yl)-2,7-dihydroxy-6-methyl-2,3-dihydro-4H-furo[3,2-c]chromene-4-one;
3-(4,7-dihydroxy-5-methyl-2-oxo-2H-chromene-3-yl)-2,7-dihydroxy-9-methyl-2,3-dihydro-4H-furo[3,2-c]chromene-4-one;
9-fluoro-3-(5-fluoro-4-hydroxy-2-oxo-2H-chromene-3-yl)-2-hydroxy-2,3-dihydro-4H-furo[3,2-c]chromene-4-one;
8-fluoro-3-(6-fluoro-4-hydroxy-2-oxo-2H-chromene-3-yl)-2-hydroxy-2,3-dihydro-4H-furo[3,2-c]chromene-4-one;
2-hydroxy-3-(4-hydroxy-6-chloro-2-oxo-2H-chromene-3-yl)-8-chloro-2,3-dihydro-4H-furo[3,2-c]chromene-4-one;
8-bromo-3-(6-bromo-4-hydroxy-2-oxo-2H-chromene-3-yl)-2-hydroxy-2,3-dihydro-4H-furo[3,2-c]chromene-4-one;
2-hydroxy-3-(4-hydroxy-6-iodo-2-oxo-2H-chromene-3-yl)-8-iodo-2,3-dihydro-4H-furo[3,2-c]chromene-4-one;
7-fluoro-3-(7-fluoro-4-hydroxy-2-oxo-2H-chromene-3-yl)-2-hydroxy-2,3-dihydro-4H-furo[3,2-c]chromene-4-one;
2-hydroxy-3-(4-hydroxy-7-chloro-2-oxo-2H-chromene-3-yl)-7-chloro-2,3-dihydro-4H-furo[3,2-c]chromene-4-one;
2-hydroxy-3-(4-hydroxy-8-chloro-2-oxo-2H-chromene-3-yl)-6-chloro-2,3-dihydro-4H-furo[3,2-c]chromene-4-one;
2-hydroxy-3-(4-hydroxy-6-chloro-7-methyl-2-oxo-2H-chromene-3-yl)-8-chloro-7-methyl-2,3-dihydro-4H-furo[3,2-c]chromene-4-one;
2-hydroxy-3-(1-hydroxy-3-oxo-3H-benzo[f]chromene-2-yl)-2,3-dihydro-4H-benzo[f]furo[3,2-c]chromene-4-one;
2-hydroxy-3-(4-hydroxy-2-oxo-2H-benzo[g]chromene-3-yl)-2,3-dihydro-4H-benzo[g]furo[3,2-c]chromene-4-one;
2-hydroxy-1-(4-hydroxy-2-oxo-2H-benzo[h]chromene-3-yl)-1,2-dihydro-11H-benzo[h]furo[3,2-c]chromene-11-one;
2-hydroxy-3-(4-hydroxy-7-methoxy-2-oxo-2H-benzo[g]chromene-2-yl)-9-methoxy-2,3-dihydro-4H-benzo[g]furo[3,2-c]chromene-4-one;
2-hydroxy-3-(4-hydroxy-9-methoxy-2-oxo-2H-benzo[g]chromene-2-yl)-7-methoxy-2,3-dihydro-4H-benzo[g]furo[3,2-c]chromene-4-one;
3-(4,9-dihydroxy-2-oxo-2H-benzo[g]chromene-2-yl)-2,7-dihydroxy-2,3-dihydro-4H-benzo[g]furo[3,2-c]chromene-4-one;
3-(4,7-dihydroxy-2-oxo-2H-benzo[g]chromene-2-yl)-2,9-dihydroxy-2,3-dihydro-4H-benzo[g]furo[3,2-c]chromene-4-one;
2-hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one;
7-ethyl-3-(7-ethyl-4-hydroxy-2-oxo-2H-chromene-3-yl)-2-hydroxy-2,3-dihydro-4H-furo[3,2-c]chromene-4-one;
6,8-dibromo-3-(6,8-dibromo-4-hydroxy-2-oxo-2H-chromene-3-yl)-2-hydroxy-2,3-dihydro-4H-furo[3,2-c]chromene-4-one;
2-hydroxy-3-(4-hydroxy-6,8-dichloro-2-oxo-2H-chromene-3-yl)-6,8-dichloro-2,3-dihydro-4H-furo[3,2-c]chromene-4-one;
8-hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one, and stereoisomers, tautomers, pharmaceutically acceptable salts and solvates thereof and a pharmaceutically acceptable diluent or carrier.

6. A method of treating a disease or condition associated with an undesirable inflammatory immune response, which comprises administering to a subject an amount of a compound
selected from the group consisting of:
- 2-hydroxy-3-(4-hydroxy-5-methyl-2-oxo-2H-chromene-3-yl)-9-methyl-2,3-dihydro-4H-furo[3,2-c]chromene-4-one;
- 2-hydroxy-3-(4-hydroxy-6-methyl-2-oxo-2H-chromene-3-yl)-8-methyl-2,3-dihydro-4H-furo[3,2-c]chromene-4-one;
- 2-hydroxy-3-(4-hydroxy-7-methyl-2-oxo-2H-chromene-3-yl)-7-methyl-2,3-dihydro-4H-furo[3,2-c]chromene-4-one;
- 2-hydroxy-3-(4-hydroxy-8-methyl-2-oxo-2H-chromene-3-yl)-6-methyl-2,3-dihydro-4H-furo[3,2-c]chromene-4-one;
- 2-hydroxy-3-(4-hydroxy-5,7-dimethyl-2-oxo-2H-chromene-3-yl)-7,9-dimethyl-2,3-dihydro-4H-furo[3,2-c]chromene-4-one;
- 2-hydroxy-3-(4-hydroxy-5,8-dimethyl-2-oxo-2H-chromene-3-yl)-6,9-dimethyl-2,3-dihydro-4H-furo[3,2-c]chromene-4-one;
- 2-hydroxy-3-(4-hydroxy-6,7-dimethyl-2-oxo-2H-chromene-3-yl)-7,8-dimethyl-2,3-dihydro-4H-furo[3,2-c]chromene-4-one;
- 2-hydroxy-3-(4-hydroxy-7,8-dimethyl-2-oxo-2H-chromene-3-yl)-6,7-dimethyl-2,3-dihydro-4H-furo[3,2-c]chromene-4-one;
- 2-hydroxy-3-(4-hydroxy-6,8-dimethyl-2-oxo-2H-chromene-3-yl)-6,8-dimethyl-2,3-dihydro-4H-furo[3,2-c]chromene-4-one;
- 8-ethyl-3-(6-ethyl-4-hydroxy-2-oxo-2H-chromene-3-yl)-2-hydroxy-2,3-dihydro-4H-furo[3,2-c]chromene-4-one;
- 6-ethyl-3-(8-ethyl-4-hydroxy-2-oxo-2H-chromene-3-yl)-2-hydroxy-2,3-dihydro-4H-furo[3,2-c]chromene-4-one;
- 2-hydroxy-3-(4-hydroxy-6-isopropyl-2-oxo-2H-chromene-3-yl)-8-isopropyl-2,3-dihydro-4H-furo[3,2-c]chromene-4-one;
- 2-hydroxy-3-(4-hydroxy-8-isopropyl-2-oxo-2H-chromene-3-yl)-6-isopropyl-2,3-dihydro-4H-furo[3,2-c]chromene-4-one;
- 2-hydroxy-3-(4-hydroxy-6,8-diisopropyl-2-oxo-2H-chromene-3-yl)-6,8-diisopropyl-2,3-dihydro-4H-furo[3,2-c]chromene-4-one;
- 2-hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one;
- 2-hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one;
- 2-hydroxy-3-(4-hydroxy-5-methoxy-2-oxo-2H-chromene-3-yl)-9-methoxy-2,3-dihydro-4H-furo[3,2-c]chromene-4-one;
- 2-hydroxy-3-(4-hydroxy-6-methoxy-2-oxo-2H-chromene-3-yl)-8-methoxy-2,3-dihydro-4H-furo[3,2-c]chromene-4-one;
- 2-hydroxy-3-(4-hydroxy-7-methoxy-2-oxo-2H-chromene-3-yl)-7-methoxy-2,3-dihydro-4H-furo[3,2-c]chromene-4-one;
- 2-hydroxy-3-(4-hydroxy-8-methoxy-2-oxo-2H-chromene-3-yl)-6-methoxy-2,3-dihydro-4H-furo[3,2-c]chromene-4-one;
- 2-hydroxy-3-(4-hydroxy-5,7-dimethoxy-2-oxo-2H-chromene-3-yl)-7,9-dimethoxy-2,3-dihydro-4H-furo[3,2-c]chromene-4-one;
- 2-hydroxy-3-(4-hydroxy-6,7-dimethoxy-2-oxo-2H-chromene-3-yl)-7,8-dimethoxy-2,3-dihydro-4H-furo[3,2-c]chromene-4-one;
- 3-(4,5-dihydroxy-2-oxo-2H-chromene-3-yl)-2,9-dihydroxy-2,3-dihydro-4H-furo[3,2-c]chromene-4-one;
- 3-(4,6-dihydroxy-2-oxo-2H-chromene-3-yl)-2,8-dihydroxy-2,3-dihydro-4H-furo[3,2-c]chromene-4-one;
- 3-(4,7-dihydroxy-8-methyl-2-oxo-2H-chromene-3-yl)-2,7-dihydroxy-6-methyl-2,3-dihydro-4H-furo[3,2-c]chromene-4-one;
- 3-(4,7-dihydroxy-5-methyl-2-oxo-2H-chromene-3-yl)-2,7-dihydroxy-9-methyl-2,3-dihydro-4H-furo[3,2-c]chromene-4-one;
- 9-fluoro-3-(5-fluoro-4-hydroxy-2-oxo-2H-chromene-3-yl)-2-hydroxy-2,3-dihydro-4H-furo[3,2-c]chromene-4-one;
- 8-fluoro-3-(6-fluoro-4-hydroxy-2-oxo-2H-chromene-3-yl)-2-hydroxy-2,3-dihydro-4H-furo[3,2-c]chromene-4-one;
- 2-hydroxy-3-(4-hydroxy-6-chloro-2-oxo-2H-chromene-3-yl)-8-chloro-2,3-dihydro-4H-furo[3,2-c]chromene-4-one;
- 8-bromo-3-(6-bromo-4-hydroxy-2-oxo-2H-chromene-3-yl)-2-hydroxy-2,3-dihydro-4H-furo[3,2-c]chromene-4-one;
- 2-hydroxy-3-(4-hydroxy-6-iodo-2-oxo-2H-chromene-3-yl)-8-iodo-2,3-dihydro-4H-furo[3,2-c]chromene-4-one;
- 7-fluoro-3-(7-fluoro-4-hydroxy-2-oxo-2H-chromene-3-yl)-2-hydroxy-2,3-dihydro-4H-furo[3,2-c]chromene-4-one;
- 2-hydroxy-3-(4-hydroxy-7-chloro-2-oxo-2H-chromene-3-yl)-7-chloro-2,3-dihydro-4H-furo[3,2-c]chromene-4-one;
- 2-hydroxy-3-(4-hydroxy-8-chloro-2-oxo-2H-chromene-3-yl)-6-chloro-2,3-dihydro-4H-furo[3,2-c]chromene-4-one;
- 2-hydroxy-3-(4-hydroxy-6-chloro-7-methyl-2-oxo-2H-chromene-3-yl)-8-chloro-7-methyl-2,3-dihydro-4H-furo[3,2-c]chromene-4-one;
- 2-hydroxy-3-(1-hydroxy-3-oxo-3H-benzo[f]chromene-2-yl)-2,3-dihydro-4H-benzo[f]furo[3,2-c]chromene-4-one;
- 2-hydroxy-3-(4-hydroxy-2-oxo-2H-benzo[g]chromene-3-yl)-2,3-dihydro-4H-benzo[g]furo[3,2-c]chromene-4-one;
- 2-hydroxy-1-(4-hydroxy-2-oxo-2H-benzo[h]chromene-3-yl)-1,2-dihydro-11H-benzo[h]furo[3,2-c]chromene-11-one;
- 2-hydroxy-3-(4-hydroxy-7-methoxy-2-oxo-2H-benzo[g]chromene-2-yl)-9-methoxy-2,3-dihydro-4H-benzo[g]furo[3,2-c]chromene-4-one;
- 2-hydroxy-3-(4-hydroxy-9-methoxy-2-oxo-2H-benzo[g]chromene-2-yl)-7-methoxy-2,3-dihydro-4H-benzo[g]furo[3,2-c]chromene-4-one;
- 3-(4,9-dihydroxy-2-oxo-2H-benzo[g]chromene-2-yl)-2,7-dihydroxy-2,3-dihydro-4H-benzo[g]furo[3,2-c]chromene-4-one;
- 3-(4,7-dihydroxy-2-oxo-2H-benzo[g]chromene-2-yl)-2,9-dihydroxy-2,3-dihydro-4H-benzo[g]furo[3,2-c]chromene-4-one;
- 2-hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one;

7-ethyl-3-(7-ethyl-4-hydroxy-2-oxo-2H-chromene-3-yl)-2-hydroxy-2,3-dihydro-4H-furo[3,2-c]chromene-4-one;

6,8-dibromo-3-(6,8-dibromo-4-hydroxy-2-oxo-2H-chromene-3-yl)-2-hydroxy-2,3-dihydro-4H-furo[3,2-c]chromene-4-one;

2-hydroxy-3-(4-hydroxy-6,8-dichloro-2-oxo-2H-chromene-3-yl)-6,8-dichloro-2,3-dihydro-4H-furo[3,2-c]chromene-4-one;

8-hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one, and stereoisomers, tautomers, pharmaceutically acceptable salts and solvates thereof, effective to reduce or inhibit said inflammatory response.

7. The method of claim 6, wherein the inflammatory disease or condition is selected from the group consisting of asthma, chronic obstructive pulmonary disease, allergic rhinitis, nasal polyps, eczema, psoriasis, allergic dermatitis, neurodermatitis, pruritis, conjunctivitis, rheumatoid arthritis, Crohn's disease, colitis and ulcerative cohtis, insulin-dependent diabetes, autoimmune thyroiditis, lupus erythematosus, multiple sclerosis, Raynaud's disease, rheumatoid spondylitis, septic arthritis, polyarthritis, retinitis, meningitis, encephalitis, acute trauma, sepsis, and glomerulonephritis.

8. A method of inhibiting granulocyte degranulation, comprising selected from the group consisting of:

2-hydroxy-3-(4-hydroxy-5-methyl-2-oxo-2H-chromene-3-yl)-9-methyl-2,3-dihydro-4H-furo[3,2-c]chromene-4-one;

2-hydroxy-3-(4-hydroxy-6-methyl-2-oxo-2H-chromene-3-yl)-8-methyl-2,3-dihydro-4H-furo[3,2-c]chromene-4-one;

2-hydroxy-3-(4-hydroxy-7-methyl-2-oxo-2H-chromene-3-yl)-7-methyl-2,3-dihydro-4H-furo[3,2-c]chromene-4-one;

2-hydroxy-3-(4-hydroxy-8-methyl-2-oxo-2H-chromene-3-yl)-6-methyl-2,3-dihydro-4H-furo[3,2-c]chromene-4-one;

2-hydroxy-3-(4-hydroxy-5,7-dimethyl-2-oxo-2H-chromene-3-yl)-7,9-dimethyl-2,3-dihydro-4H-furo[3,2-c]chromene-4-one;

2-hydroxy-3-(4-hydroxy-5,8-dimethyl-2-oxo-2H-chromene-3-yl)-6,9-dimethyl-2,3-dihydro-4H-furo[3,2-c]chromene-4-one;

2-hydroxy-3-(4-hydroxy-6,7-dimethyl-2-oxo-2H-chromene-3-yl)-7,8-dimethyl-2,3-dihydro-4H-furo[3,2-c]chromene-4-one;

2-hydroxy-3-(4-hydroxy-7,8-dimethyl-2-oxo-2H-chromene-3-yl)-6,7-dimethyl-2,3-dihydro-4H-furo[3,2-c]chromene-4-one;

2-hydroxy-3-(4-hydroxy-6,8-dimethyl-2-oxo-2H-chromene-3-yl)-6,8-dimethyl-2,3-dihydro-4H-furo[3,2-c]chromene-4-one;

8-ethyl-3-(6-ethyl-4-hydroxy-2-oxo-2H-chromene-3-yl)-2-hydroxy-2,3-dihydro-4H-furo[3,2-c]chromene-4-one;

6-ethyl-3-(8-ethyl-4-hydroxy-2-oxo-2H-chromene-3-yl)-2-hydroxy-2,3-dihydro-4H-furo[3,2-c]chromene-4-one;

2-hydroxy-3-(4-hydroxy-6-isopropyl-2-oxo-2H-chromene-3-yl)-8-isopropyl-2,3-dihydro-4H-furo[3,2-c]chromene-4-one;

2-hydroxy-3-(4-hydroxy-8-isopropyl-2-oxo-2H-chromene-3-yl)-6-isopropyl-2,3-dihydro-4H-furo[3,2-c]chromene-4-one;

2-hydroxy-3-(4-hydroxy-6,8-diisopropyl-2-oxo-2H-chromene-3-yl)-6,8-diisopropyl-2,3-dihydro-4H-furo[3,2-c]chromene-4-one;

2-hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one;

2-hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one;

2-hydroxy-3-(4-hydroxy-5-methoxy-2-oxo-2H-chromene-3-yl)-9-methoxy-2,3-dihydro-4H-furo[3,2-c]chromene-4-one;

2-hydroxy-3-(4-hydroxy-6-methoxy-2-oxo-2H-chromene-3-yl)-8-methoxy-2,3-dihydro-4H-furo[3,2-c]chromene-4-one;

2-hydroxy-3-(4-hydroxy-7-methoxy-2-oxo-2H-chromene-3-yl)-7-methoxy-2,3-dihydro-4H-furo[3,2-c]chromene-4-one;

2-hydroxy-3-(4-hydroxy-8-methoxy-2-oxo-2H-chromene-3-yl)-6-methoxy-2,3-dihydro-4H-furo[3,2-c]chromene-4-one;

2-hydroxy-3-(4-hydroxy-5,7-dimethoxy-2-oxo-2H-chromene-3-yl)-7,9-dimethoxy-2,3-dihydro-4H-furo[3,2-c]chromene-4-one;

2-hydroxy-3-(4-hydroxy-6,7-dimethoxy-2-oxo-2H-chromene-3-yl)-7,8-dimethoxy-2,3-dihydro-4H-furo[3,2-c]chromene-4-one;

3-(4,5-dihydroxy-2-oxo-2H-chromene-3-yl)-2,9-dihydroxy-2,3-dihydro-4H-furo[3,2-c]chromene-4-one;

3-(4,6-dihydroxy-2-oxo-2H-chromene-3-yl)-2,8-dihydroxy-2,3-dihydro-4H-furo[3,2-c]chromene-4-one;

3-(4,7-dihydroxy-8-methyl-2-oxo-2H-chromene-3-yl)-2,7-dihydroxy-6-methyl-2,3-dihydro-4H-furo[3,2-c]chromene-4-one;

3-(4,7-dihydroxy-5-methyl-2-oxo-2H-chromene-3-yl)-2,7-dihydroxy-9-methyl-2,3-dihydro-4H-furo[3,2-c]chromene-4-one;

9-fluoro-3-(5-fluoro-4-hydroxy-2-oxo-2H-chromene-3-yl)-2-hydroxy-2,3-dihydro-4H-furo[3,2-c]chromene-4-one;

8-fluoro-3-(6-fluoro-4-hydroxy-2-oxo-2H-chromene-3-yl)-2-hydroxy-2,3-dihydro-4H-furo[3,2-c]chromene-4-one;

2-hydroxy-3-(4-hydroxy-6-chloro-2-oxo-2H-chromene-3-yl)-8-chloro-2,3-dihydro-4H-furo[3,2-c]chromene-4-one;

8-bromo-3-(6-bromo-4-hydroxy-2-oxo-2H-chromene-3-yl)-2-hydroxy-2,3-dihydro-4H-furo[3,2-c]chromene-4-one;

2-hydroxy-3-(4-hydroxy-6-iodo-2-oxo-2H-chromene-3-yl)-8-iodo-2,3-dihydro-4H-furo[3,2-c]chromene-4-one;

7-fluoro-3-(7-fluoro-4-hydroxy-2-oxo-2H-chromene-3-yl)-2-hydroxy-2,3-dihydro-4H-furo[3,2-c]chromene-4-one;

2-hydroxy-3-(4-hydroxy-7-chloro-2-oxo-2H-chromene-3-yl)-7-chloro-2,3-dihydro-4H-furo[3,2-c]chromene-4-one;

2-hydroxy-3-(4-hydroxy-8-chloro-2-oxo-2H-chromene-3-yl)-6-chloro-2,3-dihydro-4H-furo[3,2-c]chromene-4-one;

2-hydroxy-3-(4-hydroxy-6-chloro-7-methyl-2-oxo-2H-chromene-3-yl)-8-chloro-7-methyl-2,3-dihydro-4H-furo[3,2-c]chromene-4-one;

2-hydroxy-3-(1-hydroxy-3-oxo-3H-benzo[f]chromene-2-yl)-2,3-dihydro-4H-benzo[f]furo[3,2-c]chromene-4-one;
2-hydroxy-3-(4-hydroxy-2-oxo-2H-benzo[g]chromene-3-yl)-2,3-dihydro-4H-benzo[g]furo[3,2-c]chromene-4-one;
2-hydroxy-1-(4-hydroxy-2-oxo-2H-benzo[h]chromene-3-yl)-1,2-dihydro-11H-benzo[h]furo[3,2-c]chromene-11-one;
2-hydroxy-3-(4-hydroxy-7-methoxy-2-oxo-2H-benzo[g]chromene-2-yl)-9-methoxy-2,3-dihydro-4H-benzo[g]furo[3,2-c]chromene-4-one;
2-hydroxy-3-(4-hydroxy-9-methoxy-2-oxo-2H-benzo[g]chromene-2-yl)-7-methoxy-2,3-dihydro-4H-benzo[g]furo[3,2-c]chromene-4-one;
3-(4,9-dihydroxy-2-oxo-2H-benzo[g]chromene-2-yl)-2,7-dihydroxy-2,3-dihydro-4H-benzo[g]furo[3,2-c]chromene-4-one;
3-(4,7-dihydroxy-2-oxo-2H-benzo[g]chromene-2-yl)-2,9-dihydroxy-2,3-dihydro-4H-benzo[g]furo[3,2-c]chromene-4-one;
2-hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one;
7-ethyl-3-(7-ethyl-4-hydroxy-2-oxo-2H-chromene-3-yl)-2-hydroxy-2,3-dihydro-4H-furo[3,2-c]chromene-4-one;
6,8-dibromo-3-(6,8-dibromo-4-hydroxy-2-oxo-2H-chromene-3-yl)-2-hydroxy-2,3-dihydro-4H-furo[3,2-c]chromene-4-one;
2-hydroxy-3-(4-hydroxy-6,8-dichloro-2-oxo-2H-chromene-3-yl)-6,8-dichloro-2,3-dihydro-4H-furo[3,2-c]chromene-4-one;
8-hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one, and
stereoisomers, tautomers, pharmaceutically acceptable salts and solvates thereof, effective to inhibit granulocyte degranulation.

9. A method of reducing hyperreactivity of a respiratory airway, comprising delivering to the respiratory airway of a mammal an amount of a compound
selected from the group consisting of:
2-hydroxy-3-(4-hydroxy-5-methyl-2-oxo-2H-chromene-3-yl)-9-methyl-2,3-dihydro-4H-furo[3,2-c]chromene-4-one;
2-hydroxy-3-(4-hydroxy-6-methyl-2-oxo-2H-chromene-3-yl)-8-methyl-2,3-dihydro-4H-furo[3,2-c]chromene-4-one;
2-hydroxy-3-(4-hydroxy-7-methyl-2-oxo-2H-chromene-3-yl)-7-methyl-2,3-dihydro-4H-furo[3,2-c]chromene-4-one;
2-hydroxy-3-(4-hydroxy-8-methyl-2-oxo-2H-chromene-3-yl)-6-methyl-2,3-dihydro-4H-furo[3,2-c]chromene-4-one;
2-hydroxy-3-(4-hydroxy-5,7-dimethyl-2-oxo-2H-chromene-3-yl)-7,9-dimethyl-2,3-dihydro-4H-furo[3,2-c]chromene-4-one;
2-hydroxy-3-(4-hydroxy-5,8-dimethyl-2-oxo-2H-chromene-3-yl)-6,9-dimethyl-2,3-dihydro-4H-furo[3,2-c]chromene-4-one;
2-hydroxy-3-(4-hydroxy-6,7-dimethyl-2-oxo-2H-chromene-3-yl)-7,8-dimethyl-2,3-dihydro-4H-furo[3,2-c]chromene-4-one;
2-hydroxy-3-(4-hydroxy-7,8-dimethyl-2-oxo-2H-chromene-3-yl)-6,7-dimethyl-2,3-dihydro-4H-furo[3,2-c]chromene-4-one;
2-hydroxy-3-(4-hydroxy-6,8-dimethyl-2-oxo-2H-chromene-3-yl)-6,8-dimethyl-2,3-dihydro-4H-furo[3,2-c]chromene-4-one;
8-ethyl-3-(6-ethyl-4-hydroxy-2-oxo-2H-chromene-3-yl)-2-hydroxy-2,3-dihydro-4H-furo[3,2-c]chromene-4-one;
6-ethyl-3-(8-ethyl-4-hydroxy-2-oxo-2H-chromene-3-yl)-2-hydroxy-2,3-dihydro-4H-furo[3,2-c]chromene-4-one;
2-hydroxy-3-(4-hydroxy-6-isopropyl-2-oxo-2H-chromene-3-yl)-8-isopropyl-2,3-dihydro-4H-furo[3,2-c]chromene-4-one;
2-hydroxy-3-(4-hydroxy-8-isopropyl-2-oxo-2H-chromene-3-yl)-6-isopropyl-2,3-dihydro-4H-furo[3,2-c]chromene-4-one;
2-hydroxy-3-(4-hydroxy-6,8-diisopropyl-2-oxo-2H-chromene-3-yl)-6,8-diisopropyl-2,3-dihydro-4H-furo[3,2-c]chromene-4-one;
2-hydroxy-3-(4-hydroxy-5-isopropyl-8-methyl-2-oxo-2H-chromene-3-yl)-9-isopropyl-6-methyl-2,3-dihydro-4H-furo[3,2-c]chromene-4-one;
2-hydroxy-3-(4-hydroxy-8-isopropyl-5-methyl-2-oxo-2H-chromene-3-yl)-6-isopropyl-9-methyl-2,3-dihydro-4H-furo[3,2-c]chromene-4-one;
2-hydroxy-3-(4-hydroxy-5-methoxy-2-oxo-2H-chromene-3-yl)-9-methoxy-2,3-dihydro-4H-furo[3,2-c]chromene-4-one;
2-hydroxy-3-(4-hydroxy-6-methoxy-2-oxo-2H-chromene-3-yl)-8-methoxy-2,3-dihydro-4H-furo[3,2-c]chromene-4-one;
2-hydroxy-3-(4-hydroxy-7-methoxy-2-oxo-2H-chromene-3-yl)-7-methoxy-2,3-dihydro-4H-furo[3,2-c]chromene-4-one;
2-hydroxy-3-(4-hydroxy-8-methoxy-2-oxo-2H-chromene-3-yl)-6-methoxy-2,3-dihydro-4H-furo[3,2-c]chromene-4-one;
2-hydroxy-3-(4-hydroxy-5,7-dimethoxy-2-oxo-2H-chromene-3-yl)-7,9-dimethoxy-2,3-dihydro-4H-furo[3,2-c]chromene-4-one;
2-hydroxy-3-(4-hydroxy-6,7-dimethoxy-2-oxo-2H-chromene-3-yl)-7,8-dimethoxy-2,3-dihydro-4H-furo[3,2-c]chromene-4-one;
3-(4,5-dihydroxy-2-oxo-2H-chromene-3-yl)-2,9-dihydroxy-2,3-dihydro-4H-furo[3,2-c]chromene-4-one;
3-(4,6-dihydroxy-2-oxo-2H-chromene-3-yl)-2,8-dihydroxy-2,3-dihydro-4H-furo[3,2-c]chromene-4-one;
3-(4,7-dihydroxy-8-methyl-2-oxo-2H-chromene-3-yl)-2,7-dihydroxy-6-methyl-2,3-dihydro-4H-furo[3,2-c]chromene-4-one;
3-(4,7-dihydroxy-5-methyl-2-oxo-2H-chromene-3-yl)-2,7-dihydroxy-9-methyl-2,3-dihydro-4H-furo[3,2-c]chromene-4-one;
9-fluoro-3-(5-fluoro-4-hydroxy-2-oxo-2H-chromene-3-yl)-2-hydroxy-2,3-dihydro-4H-furo[3,2-c]chromene-4-one;
8-fluoro-3-(6-fluoro-4-hydroxy-2-oxo-2H-chromene-3-yl)-2-hydroxy-2,3-dihydro-4H-furo[3,2-c]chromene-4-one;
2-hydroxy-3-(4-hydroxy-6-chloro-2-oxo-2H-chromene-3-yl)-8-chloro-2,3-dihydro-4H-furo[3,2-c]chromene-4-one;
8-bromo-3-(6-bromo-4-hydroxy-2-oxo-2H-chromene-3-yl)-2-hydroxy-2,3-dihydro-4H-furo[3,2-c]chromene-4-one;

2-hydroxy-3-(4-hydroxy-6-iodo-2-oxo-2H-chromene-3-yl)-8-iodo-2,3-dihydro-4H-furo[3,2-c]chromene-4-one;

7-fluoro-3-(7-fluoro-4-hydroxy-2-oxo-2H-chromene-3-yl)-2-hydroxy-2,3-dihydro-4H-furo[3,2-c]chromene-4-one;

2-hydroxy-3-(4-hydroxy-7-chloro-2-oxo-2H-chromene-3-yl)-7-chloro-2,3-dihydro-4H-furo[3,2-c]chromene-4-one;

2-hydroxy-3-(4-hydroxy-8-chloro-2-oxo-2H-chromene-3-yl)-6-chloro-2,3-dihydro-4H-furo[3,2-c]chromene-4-one;

2-hydroxy-3-(4-hydroxy-6-chloro-7-methyl-2-oxo-2H-chromene-3-yl)-8-chloro-7-methyl-2,3-dihydro-4H-furo[3,2-c]chromene-4-one;

2-hydroxy-3-(1-hydroxy-3-oxo-3H-benzo[f]chromene-2-yl)-2,3-dihydro-4H-benzo[f]furo[3,2-c]chromene-4-one;

2-hydroxy-3-(4-hydroxy-2-oxo-2H-benzo[g]chromene-3-yl)-2,3-dihydro-4H-benzo[g]furo[3,2-c]chromene-4-one;

2-hydroxy-1-(4-hydroxy-2-oxo-2H-benzo[h]chromene-3-yl)-1,2-dihydro-11H-benzo[h]furo[3,2-c]chromene-11-one;

2-hydroxy-3-(4-hydroxy-7-methoxy-2-oxo-2H-benzo[g]chromene-2-yl)-9-methoxy-2,3-dihydro-4H-benzo[g]furo[3,2-c]chromene-4-one;

2-hydroxy-3-(4-hydroxy-9-methoxy-2-oxo-2H-benzo[g]chromene-2-yl)-7-methoxy-2,3-dihydro-4H-benzo[g]furo[3,2-c]chromene-4-one;

3-(4,9-dihydroxy-2-oxo-2H-benzo[g]chromene-2-yl)-2,7-dihydroxy-2,3-dihydro-4H-benzo[g]furo[3,2-c]chromene-4-one;

3-(4,7-dihydroxy-2-oxo-2H-benzo[g]chromene-2-yl)-2,9-dihydroxy-2,3-dihydro-4H-benzo[g]furo[3,2-c]chromene-4-one;

2-hydroxy-3-(5-hydroxy-4,9-dimethoxy-7-oxo-7H-furo[3,2-g]chromene-6-yl)-6,10-dimethoxy-2,3-dihydro-4H-bisfuro[3,2-c;3,2-g]chromene-4-one;

7-ethyl-3-(7-ethyl-4-hydroxy-2-oxo-2H-chromene-3-yl)-2-hydroxy-2,3-dihydro-4H-furo[3,2-c]chromene-4-one;

6,8-dibromo-3-(6,8-dibromo-4-hydroxy-2-oxo-2H-chromene-3-yl)-2-hydroxy-2,3-dihydro-4H-furo[3,2-c]chromene-4-one;

2-hydroxy-3-(4-hydroxy-6,8-dichloro-2-oxo-2H-chromene-3-yl)-6,8-dichloro-2,3-dihydro-4H-furo[3,2-c]chromene-4-one;

8-hydroxy-7-(4-hydroxy-8,8-dimethyl-2-oxo-2H,7H-pyrano[2,3-h]chromene-3-yl)-2,2-dimethyl-7,8-dihydro-2H,6H-pyrano[2,3-h]furo[3,2-c]chromene-6-one, and stereoisomers, tautomers, pharmaceutically acceptable salts and solvates thereof, effective to decrease the hyperreactivity of the respiratory airway.

10. The method of claim 9, wherein the mammal is a human.

* * * * *

UNITED STATES PATENT AND TRADEMARK OFFICE
CERTIFICATE OF CORRECTION

PATENT NO. : 7,208,518 B2  Page 1 of 1
APPLICATION NO. : 11/338871
DATED : April 24, 2007
INVENTOR(S) : Mladen Mercep et al.

It is certified that error appears in the above-identified patent and that said Letters Patent is hereby corrected as shown below:

On the title page
Item (56) References Cited

Title page, Col. 2, Correction to OTHER PUBLICATIONS:

Boyd, J. et al. should read:

-- Boyd, J. et al., J. Med. Soc. "The Chemistry of the "Insoluble Red" Woods, Part II. A New Synthesis of 4-Hydroxycoumarins." 1948, pp. 174-176. --

Corrections to the Claims:

Claim 2 - Column 44, Line 1 - should read:
   -- 2. A process for preparing a compound of formula (I) --

Claim 3 - Column 46, Line 51 - should read:
   -- organic medium comprises acetonitrile. --

Claim 7 - Column 51, Line 22 - should read:
   -- tis, Chron's disease, colitis and ulcerative colitis, --

Claim 8 - Column 51, Line 30 - should read:
   -- comprising exposing mammalian granulocytes to an amount of a compound --

Signed and Sealed this

Seventeenth Day of June, 2008

JON W. DUDAS
*Director of the United States Patent and Trademark Office*